United States Patent
Eisermann et al.

(10) Patent No.: US 7,850,735 B2
(45) Date of Patent: Dec. 14, 2010

(54) ARTICULAR DISC PROSTHESIS AND METHOD FOR TREATING SPONDYLOLISTHESIS

(75) Inventors: Lukas Eisermann, Memphis, TN (US); Eddie F. Ray, III, Collierville, TN (US); Hallett Mathews, Williamsburg, VA (US); Tai Friesem, Ingleby (GB); Jean-Charles LeHuec, Pessac (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 1721 days.

(21) Appl. No.: 10/774,135

(22) Filed: Feb. 6, 2004

(65) Prior Publication Data

US 2004/0220670 A1 Nov. 4, 2004

Related U.S. Application Data

(60) Provisional application No. 60/446,963, filed on Feb. 12, 2003.

(51) Int. Cl.
*A61F 2/44* (2006.01)
(52) U.S. Cl. .................... 623/17.14; 606/279
(58) Field of Classification Search ... 623/17.11–17.16, 623/23.57; 606/61, 279
See application file for complete search history.

(56) References Cited

U.S. PATENT DOCUMENTS

| | | | |
|---|---|---|---|
| 572,486 A | 12/1896 | Horn | |
| 3,320,951 A | 5/1967 | Wittebol | |
| 3,510,883 A | 5/1970 | Cathcart | |
| 3,740,769 A | 6/1973 | Haboush | |
| 3,903,549 A | 9/1975 | Deyerle | |
| 4,309,777 A | 1/1982 | Patil | |
| 4,470,158 A | 9/1984 | Pappas et al. | |
| 4,550,450 A | 11/1985 | Kinnett | |
| 4,622,959 A | 11/1986 | Marcus | |
| 4,653,487 A | 3/1987 | Maale | |
| 4,681,589 A | 7/1987 | Tronzo | |
| 4,743,262 A | 5/1988 | Tronzo | |
| 4,759,759 A | 7/1988 | Walker et al. | |

(Continued)

FOREIGN PATENT DOCUMENTS

CH 624573 A5 8/1981

(Continued)

OTHER PUBLICATIONS

Medtronic Sofamor Danek, "Maverick Total Disc Replacement", brochure, published Dec. 2002, pp. 1-6.

(Continued)

*Primary Examiner*—Eduardo C Robert
*Assistant Examiner*—David Comstock

(57) ABSTRACT

A prosthetic device for insertion into a spondylosed intervertebral space is provided. The prosthetic device includes a first component having a first flange for longitudinally engaging a first vertebra during longitudinal insertion therein, and a second component having a second flange for longitudinally engaging a second vertebra during longitudinal insertion therein. One of the first and second components comprises a projection and the other of the first and second components comprises a recess, the projection and recess being adapted to engage one another. One of the projection and the recess are offset relative to the other of the projection and the recess to accommodate the spondylosed relationship between the first and second vertebrae.

4 Claims, 14 Drawing Sheets

U.S. PATENT DOCUMENTS

| | | | |
|---|---|---|---|
| 4,759,766 | A | 7/1988 | Buettner-Janz |
| 4,805,607 | A | 2/1989 | Engelhardt et al. |
| 4,874,389 | A | 10/1989 | Downey |
| 4,875,474 | A | 10/1989 | Border |
| 4,892,545 | A | 1/1990 | Day et al. |
| 4,932,975 | A | 6/1990 | Main et al. |
| 4,936,363 | A | 6/1990 | Schuster et al. |
| 4,946,378 | A | 8/1990 | Hirayama |
| 4,997,432 | A | 3/1991 | Keller |
| 5,004,476 | A | 4/1991 | Cook |
| 5,037,438 | A | 8/1991 | Davidson |
| 5,062,850 | A | 11/1991 | MacMillan et al. |
| 5,071,437 | A | 12/1991 | Steffee |
| 5,108,442 | A | 4/1992 | Smith |
| 5,122,130 | A | 6/1992 | Keller |
| 5,246,458 | A | 9/1993 | Graham |
| 5,258,031 | A | 11/1993 | Salib et al. |
| 5,271,737 | A | 12/1993 | Baldwin et al. |
| 5,282,868 | A | 2/1994 | Bahler |
| 5,290,312 | A | 3/1994 | Kojimoto et al. |
| 5,314,477 | A | 5/1994 | Marnay |
| 5,344,458 | A | 9/1994 | Bonutti |
| 5,401,269 | A | 3/1995 | Buettner-Janz et al. |
| 5,425,773 | A | 6/1995 | Boyd et al. |
| 5,507,816 | A | 4/1996 | Bullivant |
| 5,509,934 | A | 4/1996 | Cohen |
| 5,534,029 | A | 7/1996 | Shima |
| 5,534,030 | A | 7/1996 | Navarro et al. |
| 5,554,191 | A | 9/1996 | Lahille et al. |
| 5,556,431 | A | 9/1996 | Buettner-Janz et al. |
| 5,562,738 | A | 10/1996 | Boyd et al. |
| 5,571,109 | A | 11/1996 | Bertagnoli |
| 5,571,190 | A | 11/1996 | Ulrich et al. |
| 5,591,235 | A | 1/1997 | Kuslich |
| 5,609,638 | A | 3/1997 | Price et al. |
| 5,658,347 | A | 8/1997 | Sarkisian et al. |
| 5,674,296 | A | 10/1997 | Bryan et al. |
| 5,676,701 | A | 10/1997 | Yuan et al. |
| 5,683,394 | A | 11/1997 | Rinner |
| 5,683,465 | A | 11/1997 | Shinn et al. |
| 5,702,469 | A | 12/1997 | Whipple et al. |
| 5,755,796 | A | 5/1998 | Ibo |
| 5,755,811 | A | 5/1998 | Tanamal et al. |
| 5,782,832 | A | 7/1998 | Larsen et al. |
| 5,800,547 | A | 9/1998 | Schafer et al. |
| 5,824,094 | A | 10/1998 | Serhan et al. |
| 5,865,846 | A | 2/1999 | Bryan et al. |
| 5,888,226 | A | 3/1999 | Rogozinski |
| 5,895,428 | A | 4/1999 | Berry |
| 5,899,941 | A | 5/1999 | Nishijima et al. |
| 6,001,130 | A | 12/1999 | Bryan et al. |
| 6,010,502 | A | 1/2000 | Bagby |
| 6,019,792 | A | 2/2000 | Cauthen |
| 6,063,121 | A | 5/2000 | Xavier |
| 6,096,080 | A | 8/2000 | Nicholson et al. |
| 6,102,954 | A | 8/2000 | Albrektsson et al. |
| 6,113,637 | A | 9/2000 | Gill et al. |
| 6,113,638 | A | 9/2000 | Williams |
| 6,146,421 | A | 11/2000 | Gordon et al. |
| 6,224,607 | B1 | 5/2001 | Michelson |
| 6,228,118 | B1 | 5/2001 | Gordon |
| 6,251,140 | B1 | 6/2001 | Marino et al. |
| 6,264,655 | B1 | 7/2001 | Pisharodi |
| 6,368,350 | B1 | 4/2002 | Erickson et al. |
| 6,368,353 | B1 | 4/2002 | Arcand |
| 6,375,681 | B1 | 4/2002 | Truscott |
| 6,402,785 | B1 | 6/2002 | Zdeblick |
| 6,413,278 | B1 | 7/2002 | Marchosky |
| 6,440,139 | B2 | 8/2002 | Michelson |
| 6,517,544 | B1 | 2/2003 | Michelson |
| 6,562,045 | B2 | 5/2003 | Gil et al. |
| 6,641,614 | B1 | 11/2003 | Wagner et al. |
| 6,692,501 | B2 | 2/2004 | Michelson |
| 6,706,068 | B2 * | 3/2004 | Ferree ..................... 623/17.11 |
| 6,740,118 | B2 | 5/2004 | Eisermann et al. |
| 6,780,186 | B2 | 8/2004 | Errico et al. |
| 6,936,071 | B1 | 8/2005 | Marnay et al. |
| 2002/0077702 | A1 | 6/2002 | Castro |
| 2002/0107572 | A1 | 8/2002 | Foley et al. |
| 2002/0120270 | A1 | 8/2002 | Trieu et al. |
| 2003/0069586 | A1 | 4/2003 | Errico et al. |
| 2003/0074068 | A1 | 4/2003 | Errico |
| 2003/0097134 | A1 | 5/2003 | Kunzler |
| 2003/0176923 | A1 | 9/2003 | Keller et al. |
| 2003/0208273 | A1 | 11/2003 | Eisermann et al. |
| 2003/0236571 | A1 | 12/2003 | Ralph et al. |
| 2004/0002759 | A1 | 1/2004 | Ferree |
| 2004/0034421 | A1 | 2/2004 | Errico et al. |
| 2004/0034426 | A1 | 2/2004 | Errico et al. |
| 2004/0049279 | A1 | 3/2004 | Sevrain |
| 2004/0143332 | A1 | 7/2004 | Krueger et al. |
| 2005/0283237 | A1 | 12/2005 | Zucherman et al. |

FOREIGN PATENT DOCUMENTS

| | | |
|---|---|---|
| DE | 2804936 | 2/1979 |
| DE | 30323353 C2 | 9/1981 |
| EP | 0 560 140 | 2/1993 |
| EP | 0 560 141 | 2/1993 |
| EP | 0 747 025 | 12/1996 |
| EP | 0 820 740 | 1/1998 |
| FR | 2724108 A1 | 2/1994 |
| FR | 2718635 A1 | 4/1994 |
| FR | 2742653 A1 | 12/1995 |
| JP | 2261446 | 10/1990 |
| WO | WO 99/00074 | 1/1999 |
| WO | WO 99/05995 | 2/1999 |
| WO | WO 99/53871 | 10/1999 |
| WO | WO 00/42954 | 7/2000 |
| WO | WO 0101893 | 1/2001 |
| WO | WO 0119295 | 3/2001 |

OTHER PUBLICATIONS

Viscoglioski Bro., LLC, Spine Arthoplasty: Market Potential & Technology Update, Spine Industry Analysis Series, Nov. 2001, pp. 1-215.

Jeanette E. Ahrens, PhD, Alexis P. Shelokov, MD, Jeffrey L. Carver, BS, Normal Joint Mobility is Maintained with an Artifical Disc Prothesis, Texas Health Research Institute, Plano, Texas, HCA Columbia Hospital, Plano, Texas, Joint Biomedical Engineering Program, University of Texas Arlington, Link America, Inc., Denville NJ and Waldemar Link, Inc., Hamburg, Germany, 1999.

T. Hoogland, A. D. Steffe, J.D. Black, A.S. Greenwald, Cleveland Clinic Foundation, 24 Annual ORS Dallas, Texas, Feb. 21-23, 1978.

David S. Hungerford, M.D., Kenneth A. Krackow, M.D., Robert V. Kenna, Total Knee Arthoplasty: A Comprehensive Approach, Williams & Williams, Baltimore, MD., 1984, Chapter 5, pp. 71-88.

David S. Hungerford, M.D., and Robert V. Kenna, Preliminary Experience with a Total Knee Prothesis with Porous Coating Used Without Cement, J.B. Lippincott, Co., No. 176, Jun. 1983, pp. 95-107.

AB Swanson, GD Swanson, T Powers, MA Khalil, BK Maupin, DE Mayhew and SH Moss, The Journal of Bone & Joint Surgery: Unicompartmental and bicompartmental arthroplasty of the knee with a finned metal tibial-plateau implant, vol. 67-A, No. 8, Oct. 1995, pp. 1175-1182, The Journal of Bone & Joint Surgery, Jun. 1994.

The Journal of Bone and Joint Surgery, Sep. 1971, American Volume, vol. 53-A, No. 6, Zimmer, Warsaw, Indiana, U.S.A., Zimmer of Canada, Ltd.

The Journal of Bone and Joint Surgery, Jul. 1970, American Volume, vol. 52-A, No. 5, Zimmer, Warsaw, Indiana, U.S.A., Zimmer of Canada, Ltd.

A.H. Crenshaw, Cambell's Operative Orthopedics, Seventh Edition, vol. Two, The C.V. Mosby Company, copyright, 1987.

TH Marnay, L'Arthoplatie Intervertebral Lombaire, Orthopedic Sugeon, Kennedy Clinic, 30000 Nimes.

TH Marnay, English translation of "L'Arthoplatie Intervertebral Lombaire.", Kennedy Clinic, 30000 Nimes.

Nobou, English translation of JP 2261446.

Grosse, English translation of FR 2742653.

* cited by examiner

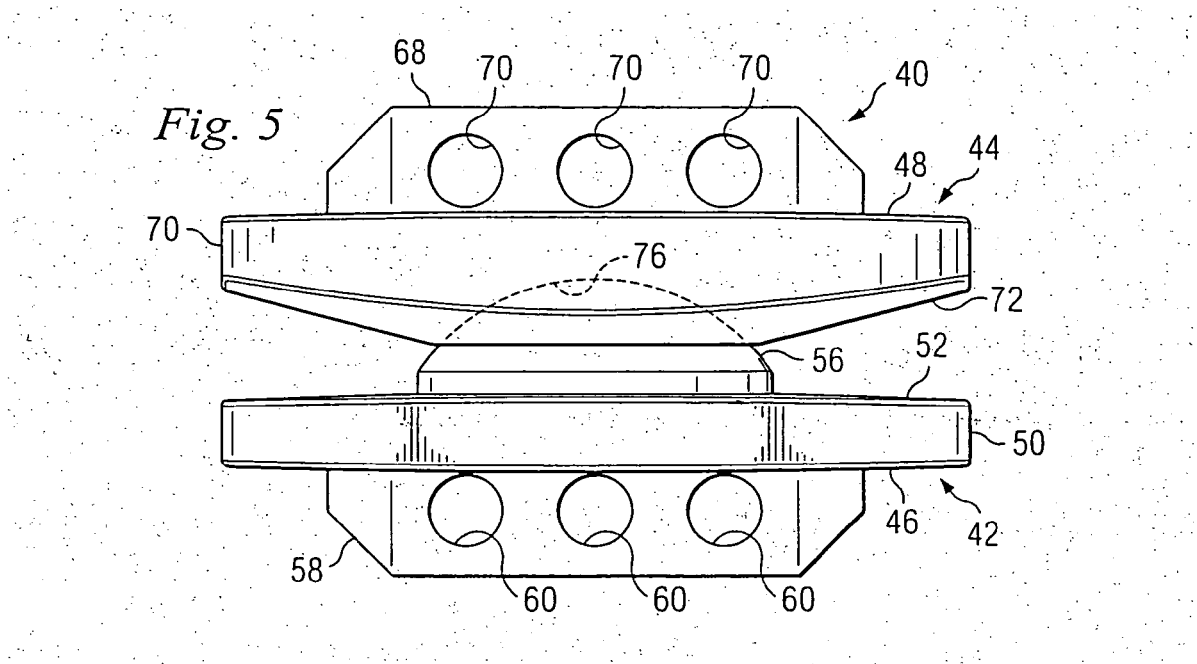
Fig. 5
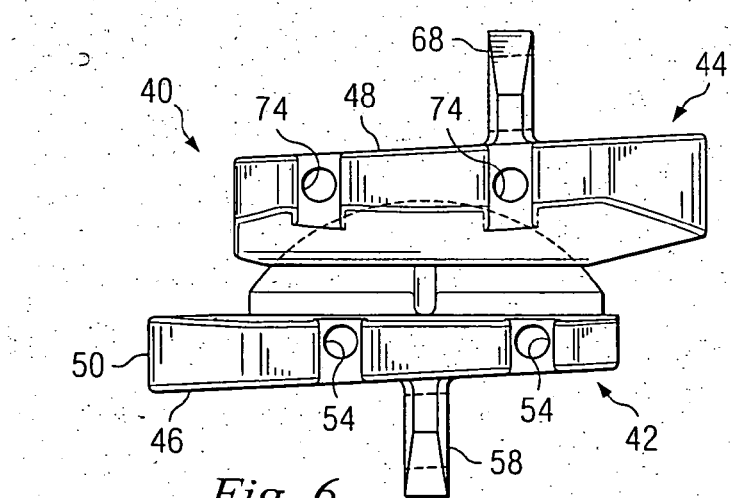
Fig. 6
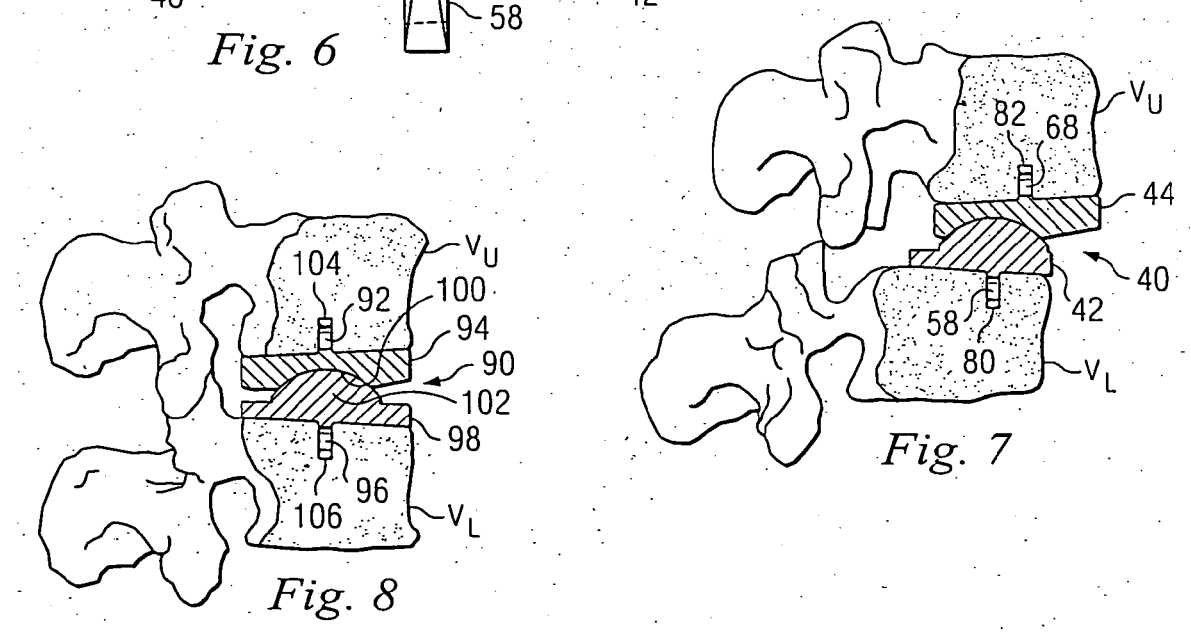
Fig. 7
Fig. 8

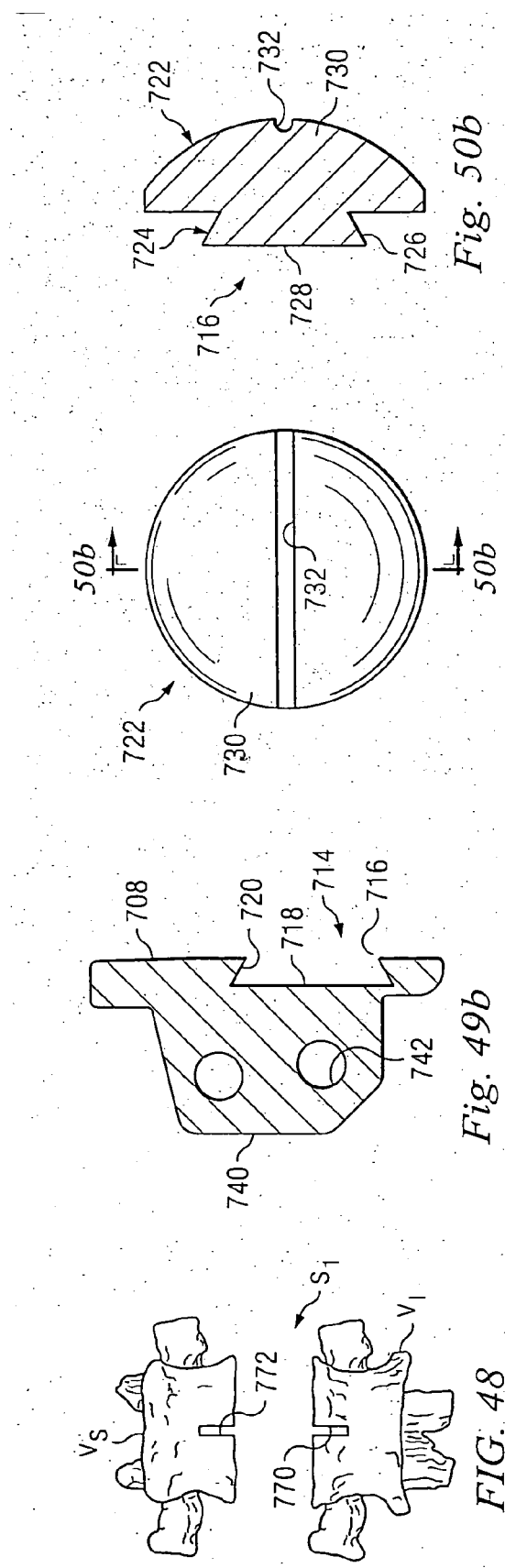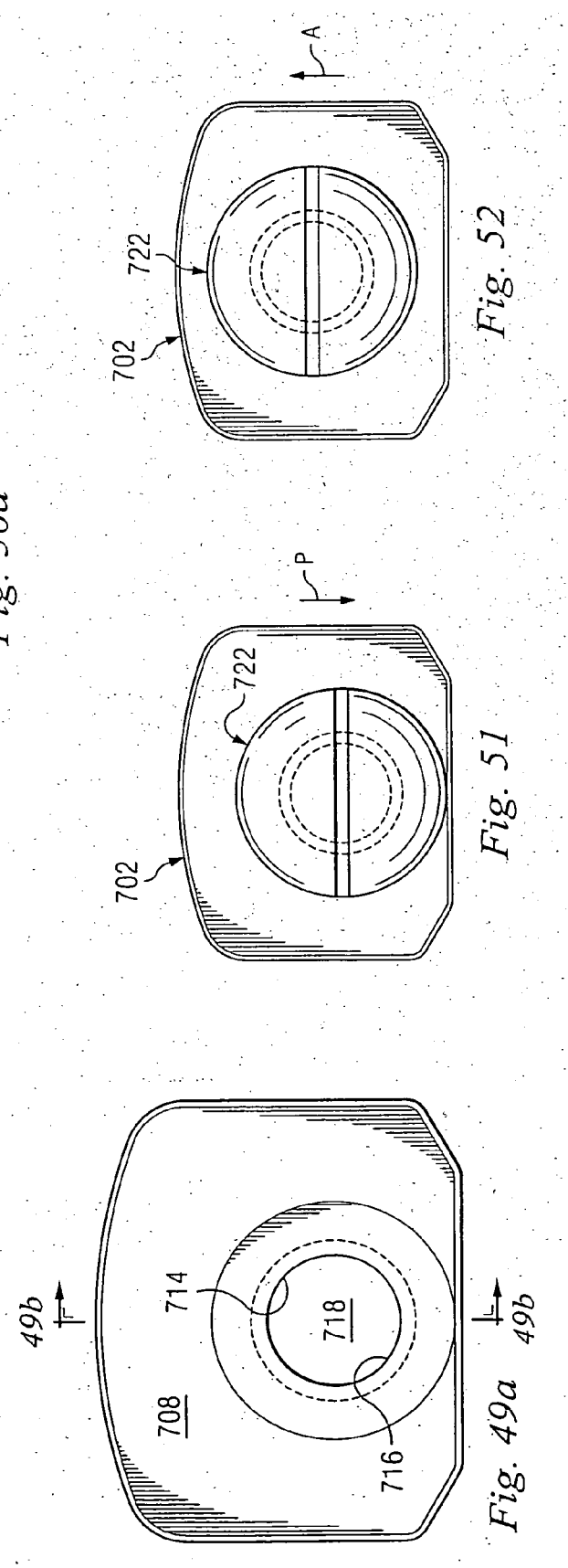

ARTICULAR DISC PROSTHESIS AND METHOD FOR TREATING SPONDYLOLISTHESIS

CROSS-REFERENCE TO RELATED APPLICATION

This application claims the benefit of U.S. Provisional Application No. 60/446,963 filed on Feb. 12, 2003. U.S. Provisional Application No. 60/446,963 is herein incorporated by reference for all legitimate purposes.

BACKGROUND

The present disclosure relates generally to the field of orthopedics and spinal surgery, and in some embodiments, the present disclosure relates to intervertebral prosthetic joints for use in the total or partial replacement of a natural intervertebral disc, and methods and tools for use therewith.

In the treatment of diseases, injuries or malformations affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are taken to ensure the proper spacing of the vertebrae formerly separated by the removed disc tissue.

In some instances, the two adjacent vertebrae are fused together using transplanted bone tissue, an artificial fusion component, or other compositions or devices. Spinal fusion procedures, however, have raised concerns in the medical community that the bio-mechanical rigidity of intervertebral fusion may predispose neighboring spinal motion segments to rapid deterioration. More specifically, unlike a natural intervertebral disc, spinal fusion prevents the fused vertebrae from pivoting and rotating with respect to one another. Such lack of mobility tends to increase stresses on adjacent spinal motion segments.

Additionally, several conditions may develop within adjacent spinal motion segments, including disc degeneration, disc herniation, instability, spinal stenosis, spondylosis and facet joint arthritis. Consequently, many patients may require additional disc removal and/or another type of surgical procedure as a result of spinal fusion. Alternatives to spinal fusion are therefore desirable.

In particular, this disclosure relates to an articulating disc prosthesis that can be inserted from the anterior approach to aid in the correction of spondylolisthesis.

SUMMARY

A prosthetic device for longitudinal insertion into an intervertebral space defined between a pair of spondylosed vertebrae is provided. The prosthetic device includes a first component, which includes a first flange longitudinally extending along a first bearing surface, and a projection extending from a first articular surface, the projection being offset relative to the first articular surface. The prosthetic device further includes a second component adapted to be engaged with the first component, the second component including a second flange longitudinally extending along a second bearing surface, the second flange being substantially aligned with the first flange upon engagement of the second component with the first component, and a recess formed in the second articular surface, the recess being offset relative to the second articular surface thereby accommodating a spondylosed relationship between a first vertebra and a second vertebra adjacent to the first vertebra. The projection and the recess engage one another to provide for articulating motion between the first and second components.

In another embodiment, a prosthetic device for insertion into an intervertebral space is provided. The prosthetic device includes a first component having a means for longitudinally engaging a first vertebra during longitudinal insertion therein, and a second component having a means for longitudinally engaging a second vertebra during longitudinal insertion therein, wherein one of the first and second components comprises a projection and the other of the first and second components comprises a recess, the projection and recess being adapted to engage one another. One of the projection and the recess is offset relative to the other of the projection and the recess.

In yet another embodiment, an arrangement for stabilizing a portion of a spondylosed spinal column is provided. The arrangement includes a prosthetic articulating device adapted to engage adjacent spondylosed vertebral bodies, the prosthetic articulating device including a first component and an offset second component, the first and second components cooperating to permit articulating motion between the first and second components. The arrangement further includes an artificial ligament disposed adjacent to the prosthetic articulating device wherein the artificial ligament engages each of the vertebral bodies.

In yet another embodiment, a method for correcting spondylolisthesis from an anterior approach is provided. The method includes providing a prosthetic device having a first articular component with an offset projection, and a second articular with an offset recess adapted to engage with the offset projection, and longitudinally inserting the first articular component into a first vertebra and longitudinally inserting the second articular component into a second vertebra, the second vertebra being adjacent to the first vertebra.

BRIEF DESCRIPTION OF THE DRAWINGS

FIG. 3b is a longitudinal, partial sectional view of the pair of adjacent vertebral bodies of FIG. 3a.

FIG. 5 is a longitudinal view of the prosthetic joint of FIG. 4a.

FIG. 6 is a lateral view of the prosthetic joint of FIG. 4a.

FIG. 7 is a lateral, partial sectional view of the prosthetic joint of FIG. 4a disposed between a pair of spondylosed vertebral endplates.

FIG. 8 is a lateral, partial sectional view of an alternative articulating prosthetic joint disposed between a pair of vertebral endplates.

FIG. 34b is a detailed view of a milling tool of the milling apparatus of FIG. 34a.

FIG. 48 is a longitudinal view of a pair of adjacent vertebral endplates.

FIG. 49a is a plan view of an articular component of the prosthetic joint of FIG. 45.

FIG. 49b is a sectional view of the articular component of FIG. 49a taken along the line 49b-49b.

FIG. 50a is a plan view of a modular projection member of the prosthetic joint of FIG. 45.

FIG. 50b is a sectional view of the modular projection member of FIG. 50a taken along the line 50b-50b.

FIG. 51 is a plan view of the modular projection member of FIG. 50a inserted into the articular component of FIG. 49a.

FIG. 52 is a plan view of the modular projection member of FIG. 50a inserted into the articular component of FIG. 49a depicting the modular projection member in a different position relative to FIG. 51.

DESCRIPTION

Figure 1:
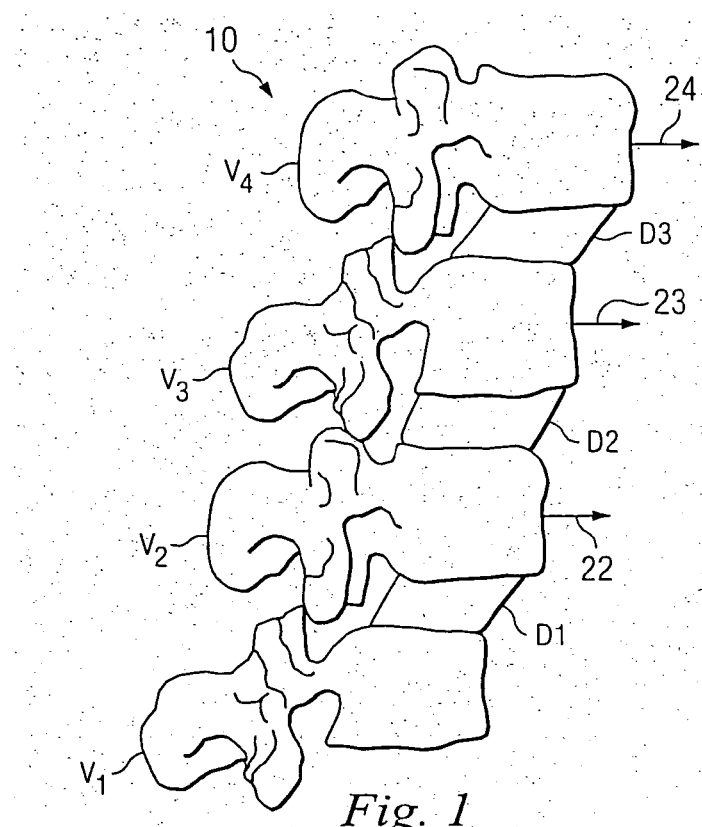
FIG. 1 is a lateral view of a portion of a spondylosed vertebral column.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. As such, individual features of separately described embodiments can be combined to form additional embodiments. In addition, examples of deformities such as spondylolisthesis are discussed; however, it is understood that the various prosthetic devices described herein can be adapted for use between not only spondylosed vertebrae, but substantially aligned vertebrae as well.

I. Lateral Correction

In many cases of deformity, such as spondylolisthesis, one or more vertebral bodies can be displaced with respect to other vertebrae or the sacrum. In such a deformity, it is desirable to reduce the extent of displacement, by re-positioning the displaced bodies from their previous position. A spondylolisthesis reduction can be a technically demanding procedure requiring great care to prevent neurological impairment and damage to surrounding soft tissue.

Referring now to FIG. 1, shown therein is a lateral view of a portion of a spinal column 10, illustrating a group of adjacent upper and lower vertebrae V1, V2, V3, V4 separated by natural intervertebral discs D1, D2, D3. The illustration of four vertebrae is only intended as an example. Another example would be a sacrum and one vertebrae.

As shown in the drawing, the vertebrae V2 is dislocated from the vertebrae V1 in a direction shown by arrow 22. Likewise, vertebrae V3 is dislocated in a direction shown by arrow 23 and vertebrae V4 is dislocated in a direction shown by arrow direction 24. It is desired that the position of vertebrae V2, V3, V4 be corrected by moving them in a direction opposite to the arrows 22, 23, 24, respectively.

Figure 2:
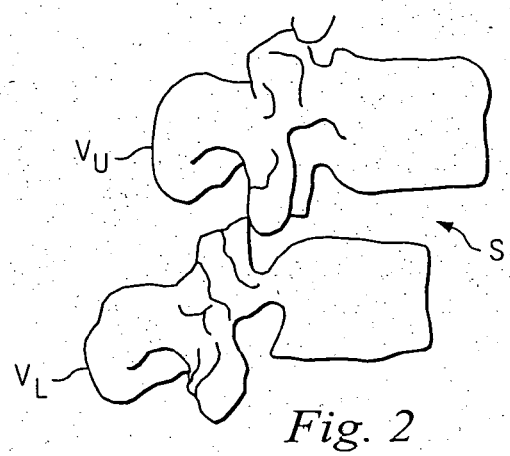
FIG. 2 is a lateral view of a pair of adjacent vertebral endplates of FIG. 1.

Referring now to FIG. 2, for the sake of further example, two of the displaced vertebrae will be discussed, designated as the lower vertebrae $V_L$ and the upper vertebrae $V_U$. In one embodiment, some or all of the natural disc that would have been positioned between the two vertebrae $V_L$, $V_U$ is typically removed via a discectomy or a similar surgical procedure, the details of which would be known to one of ordinary skill in the art. Removal of the diseased or degenerated disc results in the formation of an intervertebral space S between the upper and lower vertebrae $V_U$, $V_L$.

In the present embodiment, it is desired to insert a prosthetic joint into the intervertebral space S, similar to the prosthetic joint disclosed in U.S. Ser. No. 10/042,589 filed Jan. 9, 2002, which is incorporated by reference. However, certain changes are required of the above-referenced prosthetic joint. For the following description, the prosthetic joints discussed and described can be identical to those disclosed in the above-referenced patent application, with the exceptions discussed and suggested below.

Spondylolisthesis has not heretofore been corrected from the lateral surgical approach. However, in some instances, correction of spondylolisthesis may be desirable from a lateral approach due to the presence of vessels and/or the nervous plexus. In some embodiments, the lateral approach may be particularly pertinent when correcting spondylolisthesis in the lumbar region of the spine, although it will be understood that other regions of the spine are also contemplated.

Figure 3A:
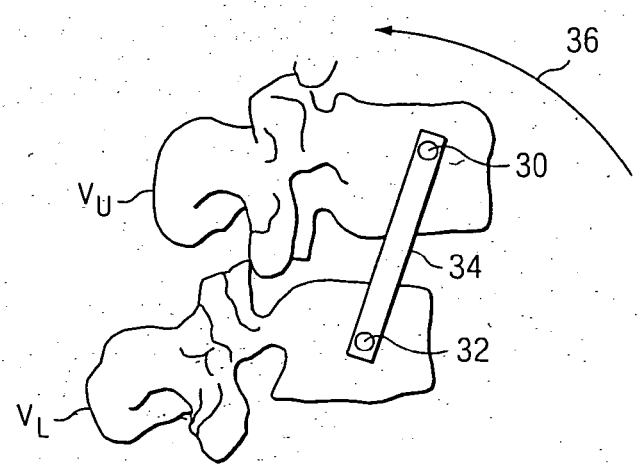
FIG. 3a is a lateral view of the pair of adjacent vertebral endplates of FIG. 2 with a rod and screw arrangement.
Figure 3B:
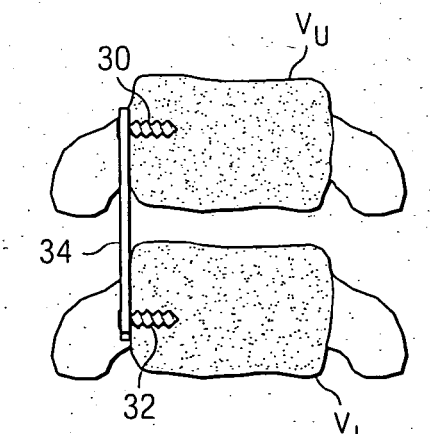

Referring to FIGS. 3a and 3b, correction of spondylolisthesis can be addressed from a lateral approach by, for example, providing a pair of bone screws 30, 32 for insertion into the vertebrae $V_U$, $V_L$, respectively. In one embodiment, the bone screws 30, 32 are bi-cortical. However, it is understood that the bone screws may alternatively be uni-cortical. Moreover, the bone screws 30, 32 may be formed of a variety of materials such as any resorbable material, titanium, and PEEK. The PEEK embodiment is advantageous due to the radiotranslucent properties resulting from the use of PEEK material. It is further understood that the bone screws 30, 32 may alternatively be of any other mechanical structure, and as such, may take the form of pins or rivets, for example. Moreover, the bone screws 30, 32 are not limited to having threaded portions to engage the vertebrae $V_U$, $V_L$.

The bone screws 30, 32 may be linked to one another via a rod 34, which is configured to rotate about both of the bone screws. It is understood that a variety of connecting members may be used other than the rod 34. For example, a non-uniform linkage member may be used to link the bone screws 30, 32. A non-uniform linkage member may provide a plurality of slots and/or grooves that can be engaged in order to aid in its rotation about the bone screws. The rod 34 may be connected prior to insertion of the bone screws 30, 32 into the vertebrae $V_U$, $V_L$, or alternatively, may be subsequently connected after placement of the screws. By applying a rotating force to the rod 34 in the direction of arrow 36, the upper vertebra $V_U$ is encouraged back into a desired position relative to the lower vertebra $V_L$. The rotating force can be applied, for example, by a rotatable wrench (not shown) that can be used by a surgeon. It is understood that the upper vertebra $V_U$ may not reach entirely to a fully corrected position in relation to the lower vertebra $V_L$, but the displacement can at least be reduced.

Although not depicted, in another embodiment, it is contemplated that the spondylosed vertebrae $V_U$, $V_L$ can be addressed from both lateral directions. Thus, a pair of bone screws substantially identical to the bone screws 30, 32 may be inserted into the vertebrae $V_U$, $V_L$ on the opposite side from and in the opposite direction to the bone screws 30, 32. In such an arrangement, the rod 34 can be replaced with a ratcheting system that engages each of the bone screw pairs, and as such, the vertebrae $V_U$, $V_L$ can be rotated relative to one another to encourage the vertebrae into a desired position relative to one another.

Still further, the rod 34 may include any number and type of engagement means to receive any number and type of rotating tools used by a surgeon. For example, a keyed connection may provide more stability when engaging the rod 34 with a corresponding rotating tool. In other examples, a clamping tool may be used and corresponding clamping notches may be formed in the rod 34 to receive the clamping tool. Such an arrangement may aid in achieving the force necessary for rotation.

Moreover, additional rods 34 and bone screws 30, 32 are contemplated for use in rotating the spondylosed vertebrae $V_U$, $V_L$ back into a desired position relative to one another. Additional rods 34 and bone screws 30, 32 may provide additional stability during the procedure.

Furthermore, although depicted as a substantially lateral insertion, the insertion of the bone screws 30, 32 into the vertebrae $V_U$, $V_L$ can be slightly angled relative to the lateral direction. Such angling of the bone screws 30, 32 during insertion may provide a preferred gripping angle from which the surgeon can begin rotation of the vertebrae $V_U$, $V_L$ relative to one another.

Figure 4A:
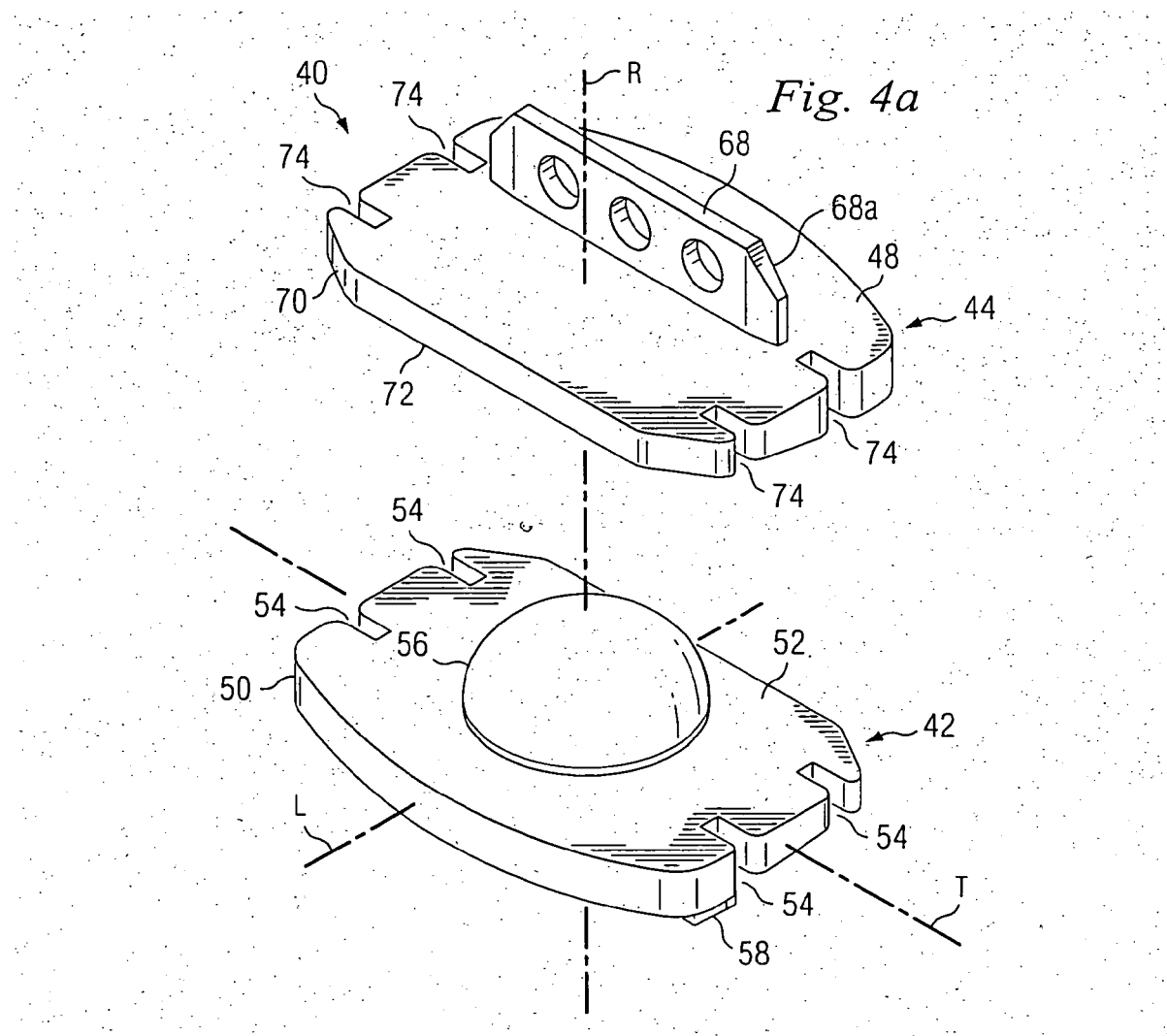
FIG. 4a is an isometric view of an articulating prosthetic joint for lateral insertion according to one embodiment of the present disclosure.

Referring to FIGS. 4a, 5, and 6, shown therein is one embodiment of an offset intervertebral articulating prosthetic joint 40 for insertion into the intervertebral space S (FIG. 2) to aid in the correction of spondylolisthesis. The articulating prosthetic joint 40 extends generally along a longitudinal axis L and includes a first articular component 42 and a second articular component 44. The articular components 42, 44 cooperate to form the prosthetic joint 40 which is sized and configured for disposition within the intervertebral space S (FIG. 2) between adjacent vertebral bodies $V_U$, $V_L$ (FIG. 2).

The prosthetic joint 40 provides relative pivotal and rotational movement between the adjacent vertebral bodies to maintain or restore motion substantially similar to the normal bio-mechanical motion provided by a natural intervertebral disc. More specifically, the articular components 42, 44 are permitted to pivot relative to one another about a number of axes, including lateral or side-to-side pivotal movement about longitudinal axis L and anterior-posterior pivotal movement about a transverse axis T. It should be understood that in one embodiment of the disclosure, the articular components 42, 44 are permitted to pivot relative to one another about any axes that lies in a plane that intersects longitudinal axis L and transverse axis T.

Furthermore, the articular components 42, 44 are permitted to rotate relative to one another about a rotational axis R. Although the prosthetic joint 40 has been illustrated and described as providing a specific combination of articulating motion, it should be understood that other combinations of articulating movement are also possible, such as, for example, relative translational or linear motion, and such movement is contemplated as falling within the scope of the present disclosure.

Although the articular components 42, 44 of prosthetic joint 40 may be formed from a wide variety of materials, in one embodiment of the disclosure, the articular components 42, 44 are formed of a cobalt-chrome-molybdenum metallic alloy (ASTM F-799 or F-75). However, in alternative embodiments of the disclosure, the articular components 42, 44 may be formed of other materials such as titanium or stainless steel, a polymeric material such as polyethylene, or any other biocompatible material that would be apparent to one of ordinary skill in the art.

The articular components 42, 44 each include a bearing surface 46, 48, respectively, that may be positioned in direct contact with vertebral bone and is preferably coated with a bone-growth promoting substance, such as, for example, a hydroxyapatite coating formed of calcium phosphate. Additionally, the bearing surfaces 46, 48 of the articular components 42, 44, respectively, may be roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

Articular component 42 includes a support plate 50 having an articular surface 52 and the opposite bearing surface 46. Support plate 50 is sized and shaped to substantially correspond to the size and shape of a vertebral endplate of the adjacent vertebral body $V_L$ (FIG. 2). The support plate 50 may include one or more notches 54 or other types of indicia for receiving or engaging with a corresponding portion of a surgical instrument (not shown) to aid in the manipulation and insertion of the prosthetic joint 40 within the intervertebral space S (FIG. 2) between the adjacent vertebral bodies $V_U, V_L$ (FIG. 2). The surgical instrument (not shown) is preferably configured to hold the articular components 42, 44 at a predetermined orientation and spatial relationship relative to one another during manipulation and insertion of the prosthetic joint 40, and to release the articular components 42, 44 once properly positioned between the adjacent vertebrae.

In one embodiment of the disclosure, the articular component 42 includes a projection 56 having a convex shape, which may be configured as a spherical-shaped ball (half of which is shown). It should be understood that other configurations of the projection 56 are also contemplated, such as, for example, cylindrical, elliptical or other arcuate configurations or possibly non-arcuate configurations. It should also be understood that the remaining portion of articular component 42 may take on planar or non-planar configurations, such as, for example, an angular or conical configuration extending about the projection 56.

A flange member or keel 58 extends from the bearing surface 46 and is configured for disposition within a preformed opening in the adjacent vertebral endplate. As with the bearing surface 46, the keel 58 may be coated with a bone-growth promoting substance, such as, for example, a hydroxyapatite coating formed of calcium phosphate. Additionally, the keel 58 maybe roughened prior to being coated with the bone-growth promoting substance to further enhance bone on-growth. In one embodiment, the keel 58 extends along the transverse axis T and is substantially centered along the bearing surface 46. However, it should be understood that other positions and orientations of the keel 58 are also contemplated.

In one embodiment, the keel 58 transversely extends along a substantial portion of the articular component 42. Such an embodiment would accommodate insertion of the prosthetic joint 40 using a lateral approach as opposed to, for example, an anterior approach. In a further embodiment, the keel 58 may be angled, tapered, or configured in some other shape to facilitate the functional demands of the keel. In still another embodiment, the keel 58 may be configured as a winged keel, including a lateral portion (not shown) extending across the main body portion of keel 58.

In one embodiment, the keel 58 includes three openings 60 extending therethrough to facilitate bone through-growth to enhance fixation to the adjacent vertebral bodies $V_U, V_L$ (FIG. 2). However, it should be understood that any number of openings 60 may be defined through the keel 58, including a single opening or two or more openings. It should also be understood that the openings 60 need not necessarily extend entirely through the keel 58, but may alternatively extend partially therethrough. It should further be understood that the keel 58 need not necessarily define any openings 60 extending either partially or entirely therethrough. Additionally, although the openings 60 are illustrated as having a circular configuration, it should be understood that other sizes and configurations of openings 60 are also contemplated.

In one embodiment, the articular component 44 includes a support plate 70 having an articular surface 72 and the opposite bearing surface 48. Support plate 70 may be sized and shaped to substantially correspond to the size and shape of a vertebral endplate of the adjacent vertebral body $V_U$. The support plate 70 may include one or more notches 74 or other types of indicia for receiving and engaging with a corresponding portion of a surgical instrument, such as discussed above with reference to articular component 42.

In one embodiment, the articular surface 72 includes a recess 76. In one embodiment, the recess 76 has a concave shape, and is configured as a spherical-shaped socket. However, it should be understood that other configurations of the recess 76 are also contemplated, such as, for example, cylindrical, elliptical or other arcuate configurations or possibly non-arcuate configurations. The remaining portion of the articular surface 72 can be angled or otherwise configured to facilitate the insertion and/or use of the prosthesis.

Although the concave recess 76 is illustrated as having a generally smooth, uninterrupted articular surface, it should be understood that a surface depression or cavity may be defined along a portion of the recess 76 to provide a means for clearing out matter, such as particulate debris, that is disposed between the abutting articular components 42, 44. In such case, the convex articular surface of the projection 56 may alternatively define a generally smooth, uninterrupted articular surface. In another embodiment, each of the convex projection 56 and the concave recess 76 may define a surface depression to facilitate removal of particulate matter disposed between the abutting articular components 42, 44.

Figure 4B:
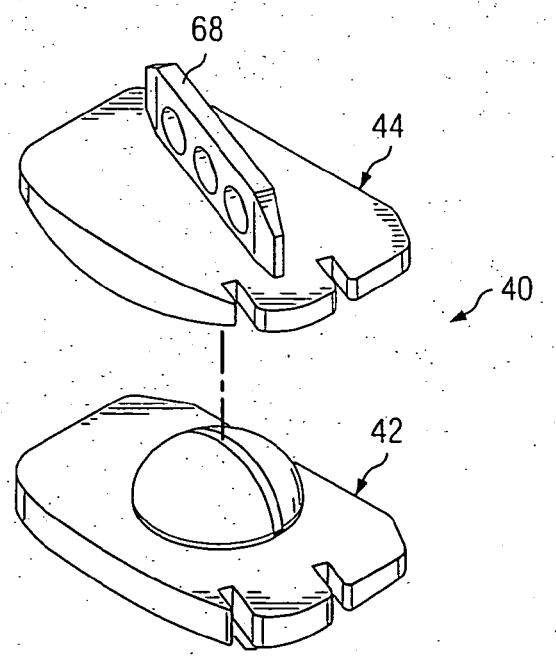
FIG. 4b is an isometric view of an articulating prosthetic joint for lateral insertion according to another embodiment of the present disclosure.
Figure 4C:
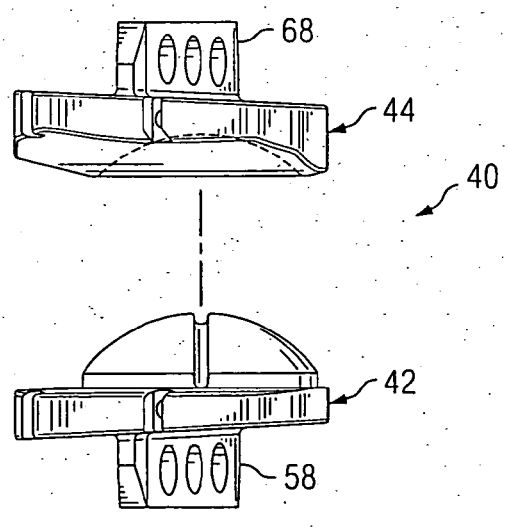
FIG. 4c is a front-view of the articulating prosthetic joint for lateral insertion of FIG. 4b.

A flange member or keel 68, configured similar to the keel 58 of articular component 42, extends from the bearing surface 48. In one embodiment, the keel 68 extends along the transverse axis T and is offset from the center of the bearing surface 48. Such an embodiment would accommodate insertion of the prosthetic joint 40 using a lateral approach. However, it should be understood that other shapes, positions and orientations of the keel 68 are also contemplated. For example, in FIGS. 4b and 4c, the keels 58 and 68 may be angled relative to the transverse axis T to aid in the circumvention of veins, arteries, bony portions, or other obstacles that may be in place during insertion of the prosthetic joint 40. Also, the keel 68 may be angled, tapered, or configured in some other shape to facilitate the functional demands of the keel. In still another embodiment, the keel 68 may be configured as a winged keel, including a transverse portion extending across the main body portion of the keel 68.

In one embodiment, and referring to FIG. 5, the keel 68 also includes three openings 70 extending therethrough to facilitate bone through-growth to enhance fixation to the adjacent vertebra. However, it should be understood that any number of openings 70 may be defined through keel 70, including a single opening or two or more openings. It should also be understood that the openings 70 need not necessarily extend entirely through the keel 68, but may alternatively extend partially therethrough. It should further be understood that the keel 68 need not necessarily define any openings 70 extending either partially or entirely therethrough. Additionally, although the openings 70 are illustrated as having a circular configuration, it should be understood that other sizes and configurations of openings 70 are also contemplated. As discussed above, the bearing surfaces 46, 48 that are in direct contact with vertebral bone are preferably coated with a bone-growth promoting substance. Specifically, the bearing surface 48 and the surface of the keel 68 can be coated with hydroxyapatite to promote bony engagement with the adjacent vertebral body $V_U$. As also discussed above, the bearing surface 48 and the surface of keel 68 can be roughened prior to application of the hydroxyapatite coating.

In some embodiments, one or both of the keels 58, 68 may include a sharp forward edge, illustrated by edge 68a of FIG. 4. By having such an edge, insertion of the keel into the associated vertebral body is facilitated. Also, the edge 68a can be of sufficient sharpness that the adjacent vertebral bodies do not require a slot for receiving the keel 68, discussed in greater detail below.

Referring to FIG. 7, to accommodate insertion of the offset prosthetic joint 40 within a spondylosed intervertebral space, the partially corrected upper and lower vertebrae $V_U$, $V_L$ can be prepared to accept the prosthetic joint 40 (shown in section in FIG. 7a) therebetween. Specifically, elongate openings or slots 80, 82 may be formed along the vertebral endplates of the upper and lower vertebrae $V_L$, $V_U$, respectively, at a predetermined width and to a predetermined depth. The slots 80, 82 can be laterally offset from each other to accommodate the displaced vertebrae $V_L$ and/or $V_U$. In one embodiment, the elongate slots 80, 82 are rectangular-shaped and extend laterally through the vertebrae $V_L$, $V_U$, respectively. In a specific embodiment, the slots 80, 82 are formed by chiseling or curetting. However, other methods of forming slots 80, 82 are also contemplated as would occur to one of ordinary skill in the art, such as, for example, by drilling or reaming. Furthermore, for some embodiments of the prosthetic joint 40, the keels 58 and/or 68 can form their own corresponding slots 80, 82, respectively.

Referring to FIG. 8, in one embodiment, the upper and lower vertebrae $V_U$, $V_L$ may be fully corrected, and thus, an alternative articulating prosthetic joint 90 may be used in correcting spondylolisthesis. The articulating joint 90 maybe substantially similar to the prosthetic joint 40 with the exception of the orientation of various elements of the articulating joint 90. For example, to accommodate insertion into fully corrected upper and lower vertebrae $V_U$, $V_L$, the articulating joint 90 may include a laterally-extending keel 92 that is substantially centered on an upper articulating component 94 of the articulating joint and a laterally-extending keel 96 that is substantially centered on a lower articulating component 98. Furthermore, the upper articulating component 94 may include a recess 100 that is substantially centered to correspond to a substantially centered projection 102 extending from the lower articulating component 98. In one embodiment, the upper and lower articulating components 94, 98 are substantially flush with one another when disposed between fully corrected upper and lower vertebrae $V_U$, $V_L$.

To accommodate insertion of the offset prosthetic joint 90, the fully corrected upper and lower vertebrae $V_U$, $V_L$ can be prepared to accept the prosthetic joint 90 therebetween. Specifically, elongate openings or slots 104, 106 may be formed along the vertebral endplates of the upper and lower vertebrae $V_U$, $V_L$, respectively, at a predetermined width and to a predetermined depth. The slots 104, 106 can be substantially aligned with each other to accommodate the fully corrected upper and lower vertebrae $V_U$, $V_L$. In one embodiment, the elongate slots 104, 106 are rectangular-shaped and extend laterally through the vertebrae $V_U$, $V_L$, respectively. In a specific embodiment, the slots 104, 106 are formed by chiseling or curetting. However, other methods of forming slots 104, 106 are also contemplated as would occur to one of ordinary skill in the art, such as, for example, by drilling or reaming. Furthermore, for some embodiments of the prosthetic joint, the keels 92 and/or 96 can form their own corresponding slots 104, 106, respectively.

Figure 9:
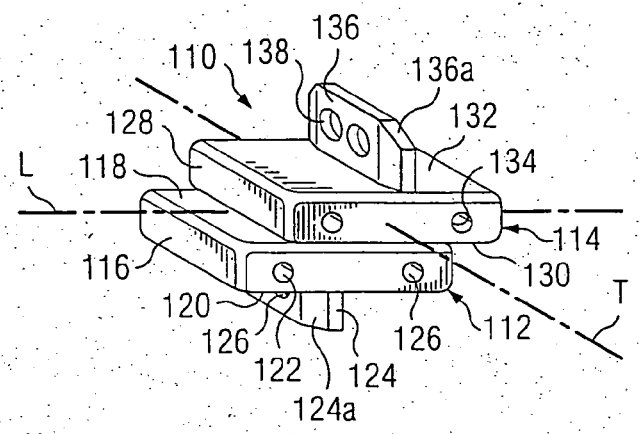
FIG. 9 is an isometric view of an alternative articulating prosthetic joint according to another embodiment of the present disclosure.

Referring to FIG. 9, in an alternative embodiment, a slidable prosthetic joint 110 can be used to help with the lateral approach for treating spondylolisthesis. The sliding joint 110 extends generally along the longitudinal axis L and includes a first slidable component 112 and a second slidable component 114. The slidable components 112, 114 cooperate to form the sliding joint 110 which is sized and configured for disposition within an intervertebral space between adjacent vertebral bodies.

The sliding joint 110 provides movement between the adjacent vertebral bodies to maintain or restore some of the motion similar to the normal bio-mechanical motion provided by a natural intervertebral disc. More specifically, the slidable components 112, 114 are permitted to translate relative to one another in the axial plane.

Although the slidable components 112, 114 of prosthetic joint 110 may be formed from a wide variety of materials, in one embodiment, the slidable components 112, 114 are formed of a cobalt-chrome-molybdenum metallic alloy (ASTM F-799 or F-75). However, in alternative embodiments, the slidable components 112, 114 may be formed of other materials such as titanium or stainless steel, a polymeric material such as polyethylene, or any other biocompatible material that would be apparent to one of ordinary skill in the art. The surfaces of the slidable components 112, 114 that are positioned in direct contact with vertebral bone are preferably coated with a bone-growth promoting substance, such as, for example, a hydroxyapatite coating formed of calcium phosphate. Additionally, the surface of the slidable components 112, 114 that are positioned in direct contact with vertebral bone are preferably roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

Slidable component 112 includes a support plate 116 having a slidable surface 118 and an opposite bearing surface 120. Support plate 116 is preferably sized and shaped to substantially correspond to the size and shape of the vertebral endplate of an adjacent vertebra. The support plate 116 can include one or more notches 122 or other types of indicia for receiving and engaging with a corresponding portion of a surgical instrument (not shown) to aid in the manipulation and insertion of the prosthetic joint 110 within an intervertebral space between adjacent vertebrae. The surgical instrument (not shown) is preferably configured to hold the slidable components 112, 114 at a predetermined orientation and spatial relationship relative to one another during manipulation and insertion of the prosthetic joint 110, and to release the slidable components 112, 114 once properly positioned between the adjacent vertebrae.

A flange member or keel 124 extends from the bearing surface 120 and is configured for disposition within a preformed opening in the adjacent vertebral endplate. In one embodiment, the keel 124 extends perpendicularly from the bearing surface 120 and is approximately centrally located along the bearing surface 120. However, it should be understood that other positions and orientations of the keel 124 are also contemplated.

In one embodiment, the keel 124 transversely extends along a substantial portion of the support plate 114. Such an embodiment would accommodate insertion of the prosthetic joint 110 using a lateral approach. In a further embodiment, the keel 124 may be angled, tapered, or configured in some other shape to facilitate the functional demands of the keel. In still another embodiment, the keel 124 may be configured as a winged keel, including a transverse portion extending across the main body portion of keel 124.

The keel 124 also includes openings 126 extending therethrough to facilitate bone through-growth to enhance fixation to the adjacent vertebra. However, it should be understood that any number of openings 126 may be defined through keel 124, including a single opening or three or more openings. It should also be understood that the openings 104 need not necessarily extend entirely through the keel 124, but may alternatively extend partially therethrough. It should further be understood that the keel 124 need not necessarily define any openings 126 extending either partially or entirely therethrough. Additionally, although the openings 126 are illustrated as having a circular configuration, it should be understood that other sizes and configurations of openings 126 are also contemplated. As discussed above, the surfaces of the slidable component 112 that are in direct contact with vertebral bone are preferably coated with a bone-growth promoting substance. Specifically, the bearing surface 120 and the surfaces of the keel 124 can be coated with hydroxyapatite to promote bony engagement with the adjacent vertebrae. As also discussed above, the bearing surface 120 and the surfaces of keel 124 can be roughened prior to application of the hydroxyapatite coating.

In one embodiment, the slidable component 114 includes a support plate 128 having a slidable surface 130 and an opposite bearing surface 132. Support plate 128 is preferably sized and shaped to substantially correspond to the size and shape of the vertebral endplate of an adjacent vertebra. The support plate 128 can include one or more notches 134 or other types of indicia for receiving and engaging with a corresponding portion of a surgical instrument, such as discussed above with reference to slidable element 112.

A flange member or keel 136, configured similar to the keel 124 of slidable component 112, extends from the bearing surface 132. In one embodiment, the keel 136 extends perpendicularly from the bearing surface 132 and is offset along the bearing surface 132 to accommodate spondylosed displacements of the vertebrae. Also, the offset position of the keel 136 helps in the circumvention of veins, arteries, bony portions, or other obstacles that may be in place during the insertion of the joint 110. It should be further understood that other positions, shapes, orientations, and quantities of the keel 136 are also contemplated. It should also be understood that the keel 136 may also be differently positioned, shaped or oriented, or more keels 136 can be used, for similar or additional reasons.

In one embodiment, the keel 136 transversely extends along a substantial portion of the support plate 128. Such an embodiment would accommodate insertion of the prosthetic joint 110 using a lateral approach as opposed to another approach such as an anterior approach. In a further embodiment, the keel 136 may be angled, tapered, or configured in some other shape to facilitate the functional demands of the keel. In still another embodiment, the keel 136 may be configured as a winged keel, including a transverse portion extending across the main body portion of keel 136.

The keel 136 also includes three openings 138 extending therethrough to facilitate bone through-growth to enhance fixation to the adjacent vertebra. However, it should be understood that any number of openings 138 may be defined through keel 136, including a single opening or three or more openings. It should also be understood that the openings 138 need not necessarily extend entirely through the keel 136, but may alternatively extend partially therethrough. It should further be understood that the keel 136 need not necessarily define any openings 138 extending either partially or entirely therethrough. Additionally, although the openings 138 are illustrated as having a circular configuration, it should be understood that other sizes and configurations of openings 138 are also contemplated. As discussed above, the surfaces of the slidable component 114 that are in direct contact with vertebral bone are preferably coated with a bone-growth promoting substance. Specifically, the bearing surface 132 and the surfaces of the keel 136 can be coated with hydroxyapatite to promote bony engagement with the adjacent vertebrae. As also discussed above, the bearing surface 132 and the surfaces of keel 136 can be roughened prior to application of the hydroxyapatite coating.

In some embodiments, one or both of the keels 124, 136 may include a sharp forward edge, illustrated by edges 124a, 136a. By having such an edge, insertion of the keels 124, 136 into the associated vertebral body is facilitated. Also, the edges 124a, 136a can be of sufficient sharpness that the vertebral body does not require a slot for receiving the keels 124, 136, respectively, discussed in greater detail below.

Figure 10:
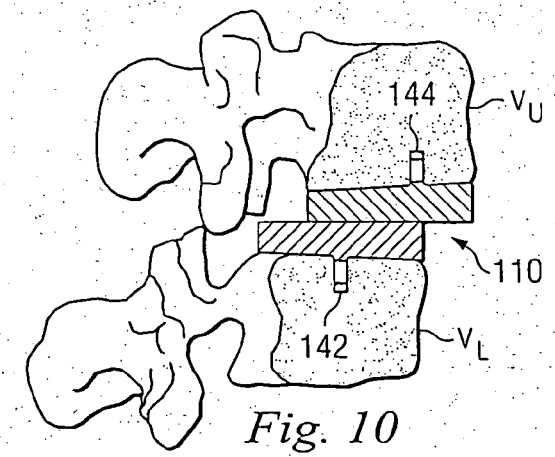
FIG. 10 is a lateral, partial sectional view of the prosthetic joint of FIG. 9 disposed between a pair of spondylosed vertebral endplates.

Referring to FIG. 10, to accommodate insertion of the prosthetic joint 110 within a spondylosed intervertebral space, the lower and upper vertebrae $V_L$, $V_U$ can be prepared to accept the prosthetic joint 110 therebetween. Specifically, elongate openings or slots 142, 144, may be formed along the vertebral endplates of the lower and upper vertebrae $V_L$, $V_U$, respectively, at a predetermined width and to a predetermined depth. The slots 142, 144 can be laterally offset from each other to accommodate the displaced vertebrae $V_L$ and/or $V_U$. In one embodiment of the disclosure, the elongate slots 142, 144 are rectangular-shaped and extend laterally through the vertebrae $V_L$, $V_U$. In a specific embodiment, the slots 142, 144 are formed by chiseling or curetting. However, other methods of forming slots 142, 144 are also contemplated as would occur to one of ordinary skill in the art, such as, for example, by drilling or reaming. Furthermore, for some embodiments of the prosthetic joint, the keels 124 and/or 136 can form their own corresponding slots.

Figure 11:
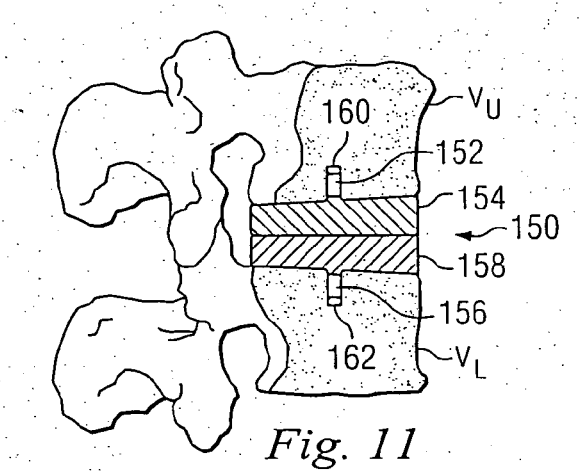
FIG. 11 is a lateral, partial sectional view of an alternative articulating prosthetic joint disposed between a pair of vertebral endplates.

Referring to FIG. 11, in one embodiment, the upper and lower vertebrae $V_U$, $V_L$ may be fully corrected, and thus, an alternative articulating joint 150 may be used in correcting spondylolisthesis. The articulating joint 150 may be substantially similar to the articulating joint 110 with the exception of the orientation of the keel. For example, to accommodate insertion into fully corrected upper and lower vertebrae $V_U$, $V_L$, the articulating joint 150 may include a keel 152 that is substantially centered on an upper articulating component 154 of the articulating joint and a keel 156 that is substantially centered on a lower articulating component 158. In one embodiment, the upper and lower articulating components 154, 158 are substantially flush with one another when disposed between fully corrected upper and lower vertebrae $V_U$, $V_L$.

To accommodate insertion of the offset prosthetic joint 150, the fully corrected upper and lower vertebrae $V_U$, $V_L$ can be prepared to accept the prosthetic joint 150 therebetween. Specifically, elongate openings or slots 160, 162 are formed along the vertebral endplates of the upper and lower vertebrae $V_U$, $V_L$, at a predetermined width and to a predetermined depth. The slots 160, 162 can be substantially aligned with each other to accommodate the fully corrected upper and lower vertebrae $V_U$, $V_L$. In one embodiment, the elongate slots 160, 162 are rectangular-shaped and extend laterally through the vertebrae $V_U$, $V_L$, respectively. In a specific embodiment, the slots 160, 162 are formed by chiseling or curetting. However, other methods of forming slots 160, 162 are also contemplated as would occur to one of ordinary skill in the art, such as, for example, by drilling or reaming. Furthermore, for some embodiments of the prosthetic joint, the keels 152 and/or 156 can form their own corresponding slots 160, 162, respectively.

Figure 12:
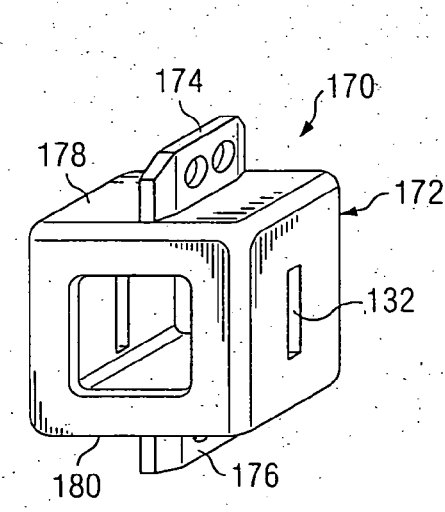
FIG. 12 is an isometric view of a disc prosthesis according to another embodiment of the present disclosure.
Figure 13:
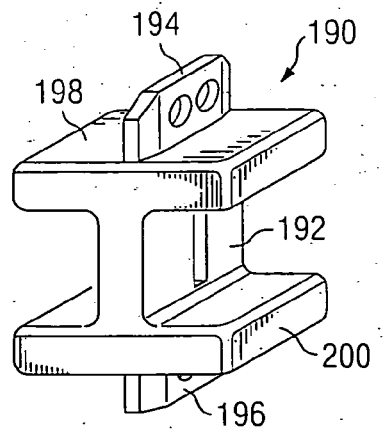
FIG. 13 is an isometric view of an alternative disc prosthesis according to another embodiment of the present disclosure.

Referring to FIGS. 12 and 13, fusion plates and cages can also be outfitted with one or more keels and laterally inserted, in a manner consistent with the motion-preserving embodiments discussed above and superior to conventional fusion arrangements. Referring specifically to FIG. 12, a lateral prosthesis 170 includes a cage 172, an upper keel 174, and a lower keel 176. The cage 172 connects to the upper and lower keels 174, 176 through support plates 178, 180, respectively. The cage 172 can include many features of the LT-CAGE™ lumbar tapered fusion device provided by Medtronic Sofamor Danek of Memphis, Tenn., and can be used to contain biological material and/or other bone growth promoting materials. Also, the lateral keels 174, 176 can help to maintain the corrected vertebrae displacement while fusion is occurring.

Referring to FIG. 13, a prosthesis 190 includes a plate 192, an upper keel 194, a lower keel 196, an upper support plate 198, and a lower support plate 200. The plate 192 can be used to maintain a desired distance between the two support plates 198, 200 and promote fusion. Since the plate 192 can be relatively thin, the remainder of the disc space can be filled with biological material, bone material, and or other bone growth promoting materials.

II. Anterior Correction

Figure 14:
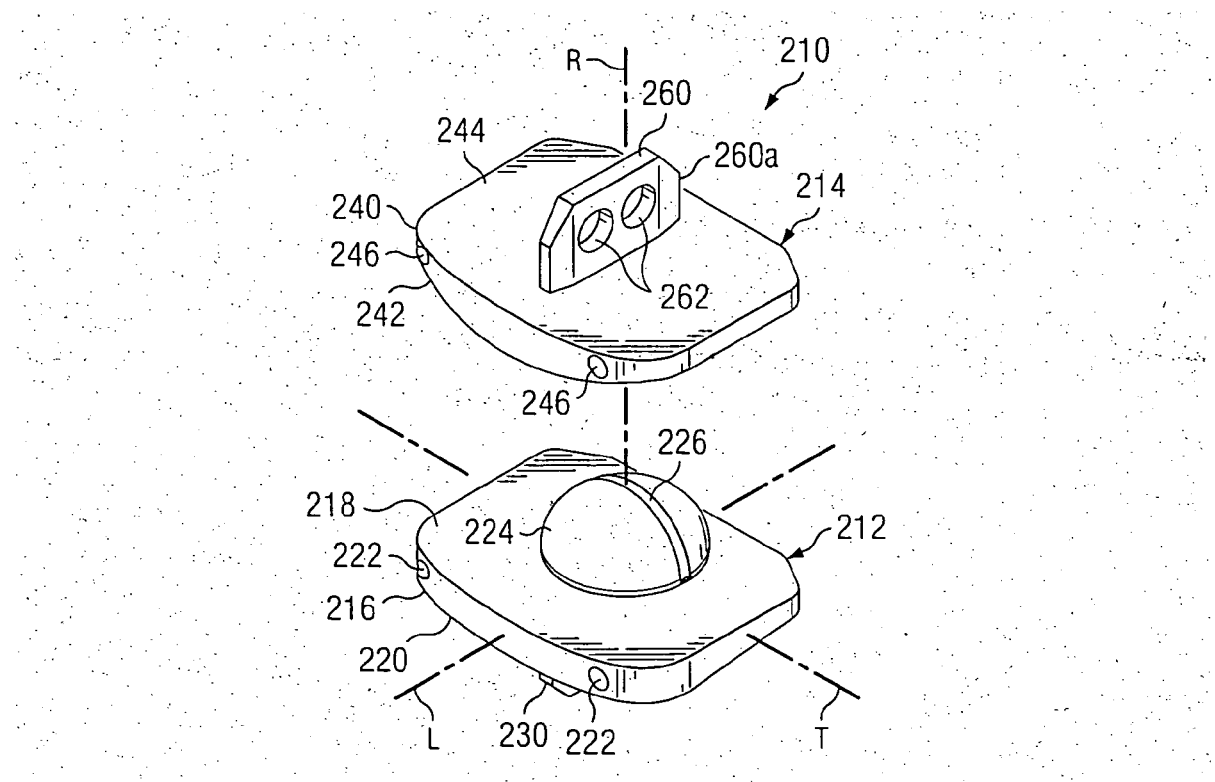
FIG. 14 is an isometric view of an alternative articulating prosthetic joint for anterior insertion according to another embodiment of the present disclosure.
Figure 15:
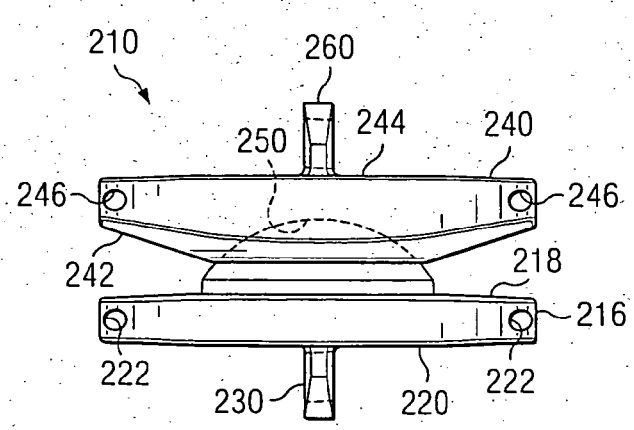
FIG. 15 is a longitudinal view of the prosthetic joint of FIG. 14.
Figure 16:
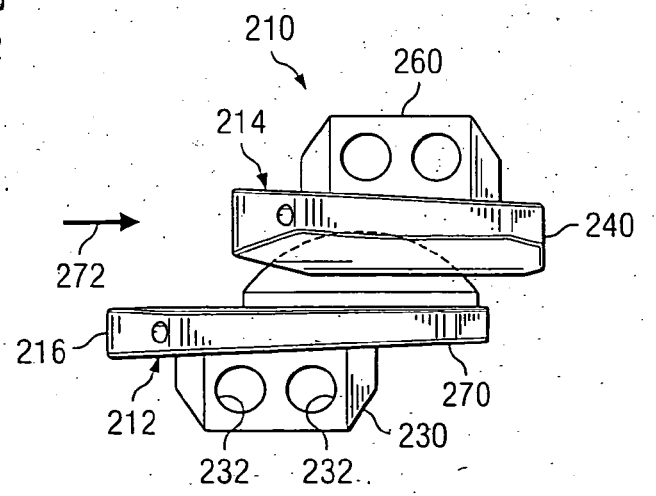
FIG. 16 is a lateral view of the prosthetic joint of FIG. 14.

In some instances, correction of spondylolisthesis may be desirable from the anterior approach. Referring to FIGS. 14-16, shown therein is an intervertebral articulating prosthetic joint 210 according to an alternative embodiment of the present disclosure. The prosthetic joint 210 extends generally along a longitudinal axis L and includes a first articular component 212 and a second articular component 214. The articular components 212, 214 cooperate to form the articulating joint 210 which is sized and configured for disposition within an intervertebral space between a pair of vertebral bodies, such as the intervertebral space S between the adjacent vertebral bodies $V_U$, $V_L$.

The prosthetic joint 210 provides relative pivotal and rotational movement between the adjacent vertebral bodies $V_U$, $V_L$ to maintain or restore motion substantially similar to the normal bio-mechanical motion provided by a natural intervertebral disc. More specifically, the articular components 212, 214 are permitted to pivot relative to one another about a number of axes, including lateral or side-to-side pivotal movement about longitudinal axis L and anterior-posterior pivotal movement about a transverse axis T. It should be understood that in one embodiment, the articular components 212, 214 are permitted to pivot relative to one another about any axes that lies in a plane that intersects longitudinal axis L and transverse axis T. Additionally, the articular components 212, 214 are permitted to rotate relative to one another about a rotational axis R. Although the prosthetic joint 210 has been illustrated and described as providing a specific combination of articulating motion, it should be understood that other combinations of articulating movement are also possible, such as, for example, relative translational or linear motion, and are contemplated as falling within the scope of the present disclosure.

Although the articular components 212, 214 of prosthetic joint 210 may be formed from a wide variety of materials, in one embodiment, the articular components 212, 214 are formed of a cobalt-chrome-molybdenum metallic alloy (ASTM F-799 or F-75). However, in alternative embodiments, the articular components 212, 214 may be formed of other materials such as titanium or stainless steel, a polymeric material such as polyethylene, or any other biocompatible material that would be apparent to one of ordinary skill in the art. The surfaces of the articular components 212, 214 that are positioned in direct contact with vertebral bone may be coated with a bone-growth promoting substance, such as, for example, a hydroxyapatite coating formed of calcium phosphate. Additionally, the surface of the articular components 212, 214 that are positioned in direct contact with vertebral bone may be roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

Articular component 212 includes a support plate 216 having an articular surface 218 and an opposite bearing surface 220. Support plate 216 may be sized and shaped to substantially correspond to the size and shape of the vertebral endplate of an adjacent vertebra. The support plate 216 can include one or more notches 222 or other types of indicia for receiving and engaging with a corresponding portion of a surgical instrument (not shown) to aid in the manipulation and insertion of the articulating joint 210 within an intervertebral space between adjacent vertebrae. The surgical instrument (not shown) is preferably configured to hold the articular components 212, 214 at a predetermined orientation and spatial relationship relative to one another during manipulation and insertion of the articulating joint 210, and to release the articular components 212, 214 once properly positioned between the adjacent vertebrae.

In one embodiment, the articular surface 218 includes a projection 224 having a convex shape, which may be configured as a spherical-shaped ball (half of which is shown). It should be understood that other configurations of the projection 224 are also contemplated, such as, for example, cylindrical, elliptical or other arcuate configurations or possibly non-arcuate configurations. It should also be understood that the remaining portion of articular surface 218 may take on planar or non-planar configurations, such as, for example, an angular or conical configuration extending about the projection 224.

In one embodiment, the convex articular surface of the projection 224 is interrupted by a surface depression or cavity 226 extending along the projection 224. In one embodiment, the surface depression 226 is configured as a groove. However, it should be understood that other types of surface depressions are also contemplated, including no depression at all. One purpose of the groove 226 is to facilitate the removal of matter disposed between abutting portions of the articular components 212, 214. More specifically, the groove 226 may aid in clearing out matter such as, for example, particulate material, that is disposed between the abutting articular surfaces of components 212, 214.

A flange member or keel 230 extends from the bearing surface 220 and is configured for disposition within a preformed opening in the adjacent vertebral endplate. In one embodiment, the keel 230 extends perpendicularly from the bearing surface 220 and is approximately centrally located along the bearing surface 220. However, it should be understood that other positions and orientations of the keel 230 are also contemplated.

In one embodiment, the keel 230 extends along substantially the entire length of the support plate 216. Such an embodiment would accommodate insertion of the articulating joint 210 using an anterior approach. In a further embodiment, the keel 230 may be angled, tapered, or configured in some other shape to facilitate the functional demands of the keel. In still another embodiment, the keel 230 may be configured as a winged keel, including a transverse portion (not shown) extending across the main body portion of keel 230.

The keel 230 also includes a pair of openings 232 extending therethrough to facilitate bone through-growth to enhance fixation to the adjacent vertebra. However, it should be understood that any number of openings 232 may be defined through keel 230, including a single opening or three or more openings. It should also be understood that the openings 232 need not necessarily extend entirely through the keel 230, but may alternatively extend partially therethrough. It should further be understood that the keel 230 need not necessarily define any openings 232 extending either partially or entirely therethrough. Additionally, although the openings 232 are illustrated as having a circular configuration, it should be understood that other sizes and configurations of the openings 232 are also contemplated. As discussed above, the surfaces of the articular component 212 that are in direct contact with vertebral bone are preferably coated with a bone-growth promoting substance. Specifically, the bearing surface 220 and the surfaces of the keel 230 can be coated with hydroxyapatite to promote bony engagement with the adjacent vertebrae. As also discussed above, the bearing surface 220 and the surfaces of keel 230 can be roughened prior to application of the hydroxyapatite coating.

In one embodiment, the articular component 214 includes a support plate 240 having an articular surface 242 and an opposite bearing surface 244. Support plate 240 may be sized and shaped to substantially correspond to the size and shape of the vertebral endplate of an adjacent vertebra. The support plate 240 can include one or more notches 246 or other types of indicia for receiving and engaging with a corresponding portion of a surgical instrument, such as discussed above with reference to articular component 212.

In one embodiment, the articular surface 242 includes a recess 250, which has a convex shape, such as that of a spherical-shaped socket. However, it should be understood that other configurations of the recess 250 are also contemplated, such as, for example, cylindrical, elliptical or other arcuate configurations or possibly non-arcuate configurations. The remaining portion of the articular surface 242 can be angled or otherwise configured to facilitate the insertion and/or use of the articulating joint 210.

Although the concave recess 250 is illustrated as having a generally smooth, uninterrupted articular surface, it should be understood that a surface depression or cavity may be defined along a portion of the recess 250 to aid in clearing out matter, such as particulate debris, that is disposed between the abutting articular surfaces of articular components 212, 214. In such case, the convex articular surface of the ball 224 may alternatively define a generally smooth, uninterrupted articular surface. In another embodiment, each of the convex projection 224 and the concave recess 250 may define a surface depression to facilitate removal of particulate matter disposed between the abutting articular surfaces.

A flange member or keel 260, configured similar to the keel 230 of articular component 212, extends from the bearing surface 244. In one embodiment, the keel 260 extends perpendicularly from the bearing surface 244 and is approximately centrally located along bearing surface 244. However, it should be understood that other positions and orientations of the keel 260 are also contemplated. It should also be understood that the articular component 214 may include two or more keels 260 extending from the bearing surface 244.

In one embodiment, the keel 260 extends along substantially the entire length of the support plate 240. Such an embodiment would accommodate insertion of the prosthetic joint 210 using an anterior approach. In a further embodiment, the keel 260 may be angled, tapered, or configured in some other shape to facilitate the functional demands of the keel. In still another embodiment, the keel 260 may be configured as a winged keel, including a transverse portion (not shown) extending across the main body portion of keel 260.

The keel 260 also includes a pair of openings 262 extending therethrough to facilitate bone through-growth to enhance fixation to the adjacent vertebra. However, it should be understood that any number of openings 262 may be defined through keel 260, including a single opening or three or more openings. It should also be understood that the openings 262 need not necessarily extend entirely through the keel 260, but may alternatively extend partially therethrough. It should further be understood that the keel 260 need not necessarily define any openings 262 extending either partially or entirely therethrough. Additionally, although the openings 262 are illustrated as having a circular configuration, it should be understood that other sizes and configurations of openings 262 are also contemplated. As discussed above, the surfaces of the articular component 214 that are in direct contact with vertebral bone are preferably coated with a bone-growth promoting substance. Specifically, the bearing surface 244 and the surfaces of the keel 260 can be coated with hydroxyapatite to promote bony engagement with the adjacent vertebrae. As also discussed above, the bearing surface 244 and the surfaces of keel 260 can be roughened prior to application of the hydroxyapatite coating.

In some embodiments, one or both of the keels 230, 260 may include a sharp forward edge, illustrated by edge 260a of FIG. 14. By having such an edge, insertion of the keel into the associated vertebral body is facilitated. Also, the edge 260a can be of sufficient sharpness that the vertebral body does not require a slot for receiving the keel 260, discussed in greater detail below.

To work with dislocated vertebrae, such as vertebrae V1-V5 of FIG. 1 associated with spondylolisthesis, it is recognized that the task of fully correcting and aligning a spondylosed segment may not be achievable or desirable by the surgeon. Therefore, the basic articulation described in co-pending and presently incorporated U.S. Ser. No. 10/042,589 now has an associated displacement to correspond to the vertebrae displacement. That is, for the amount of displacement between two adjacent spondylosed vertebrae, the articulation of the prosthetic joint 210 is made to correspond thereto. In some embodiments, such displacement can be effected by positioning one or more of the projection 224 in an offset position on the articular surface 218 of the articular component 212, and positioning one or more of the recess 250 in an offset position on the articular surface 242 of the articular component 214. This allows an uncorrected or partially corrected displacement to be mobilized.

Figure 17:
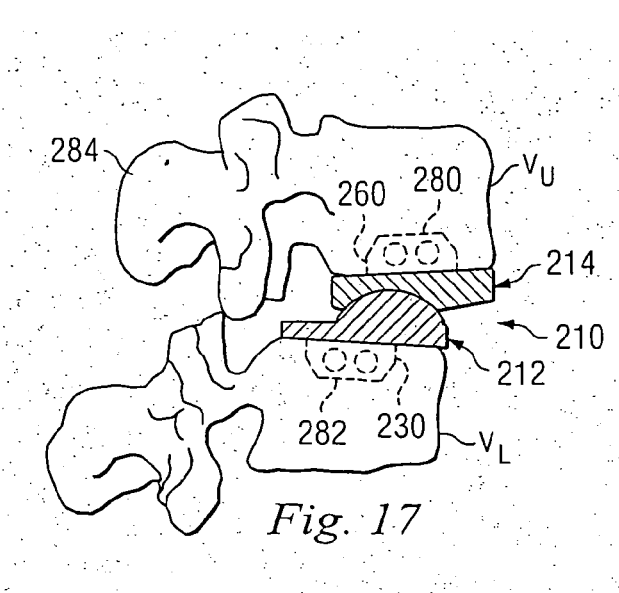
FIG. 17 is a lateral view of the prosthetic joint of FIG. 14 disposed between a pair of spondylosed vertebral endplates.

More particularly, and referring to FIGS. 14 and 17, the projection 224 is offset relative to the articular surface 218. For example, when the lower vertebra ($V_L$ of FIG. 17) is offset in the posterior direction (illustrated by arrow P in FIG. 17), the articular component 212 may be configured such that the projection 224 is offset in the anterior direction relative to the articular surface 218. Continuing this example, the upper vertebra $V_U$ is therefore offset from the lower vertebra $V_L$ in the anterior direction (illustrated by arrow A in FIG. 17), and thus, the articular component 214 may be configured such that the recess 250 is offset in the posterior direction relative to the articular surface 242. In this manner, the articular components 212, 214 can be configured to engage one another via the projection 224 and the recess 250, yet be offset from one another to accommodate the spondylosed relationship of the upper and lower vertebrae $V_U$, $V_L$ of FIG. 17.

Referring now to FIG. 16, in another embodiment, the articulating joint 210 may be modified such that the support plate 216 includes an extended section 270 to accommodate a more pronounced displacement relative to FIG. 17 (illustrated by arrow 272) and/or provide additional stability against subluxation. The projection 224 may be positioned on the extended section 270 to provide for the more pronounced displacement between articular components 212, 214.

Referring to, FIGS 2 and 17, to accommodate insertion of the prosthetic joint 210 within the intervertebral space S, the upper and lower vertebrae $V_U$, $V_L$ can be prepared to accept the prosthetic joint 210 therebetween. Specifically, elongate openings or slots 280, 282 are formed along the vertebral endplates of the upper and lower vertebrae $V_U$, $V_L$, respectively, at a predetermined width and to a predetermined depth. In one embodiment, the elongate slots 280, 282 are rectangular-shaped and extend from an anterior side 284 of the vertebrae $V_U$, $V_L$ toward a posterior side. In a specific embodiment, the slots 280, 282 are formed by chiseling or curetting. However, other methods of forming the slots 280, 282 are also contemplated as would occur to one of ordinary skill in the art, such as, for example, by drilling or reaming. Furthermore, for some embodiments of the prosthetic joint 210, the keels 230 and/or 260 can form their own corresponding slots 280, 282, respectively. The preparation and example sizes of the slots 280, 282 are described in further detail in co-pending and presently incorporated U.S. Ser. No. 10/042,589.

Figure 18:
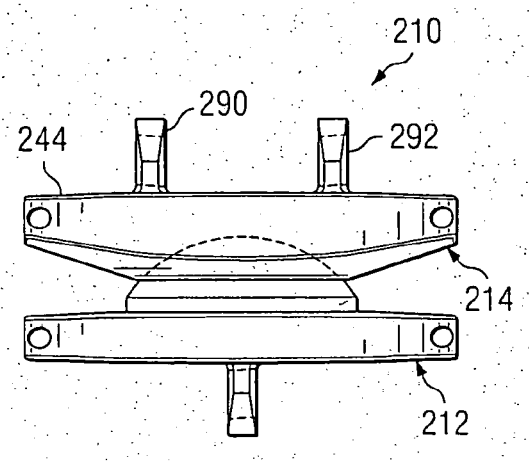
FIG. 18 is a longitudinal view of an alternative articulating prosthetic joint for anterior insertion according to another embodiment of the present disclosure.
Figure 19:
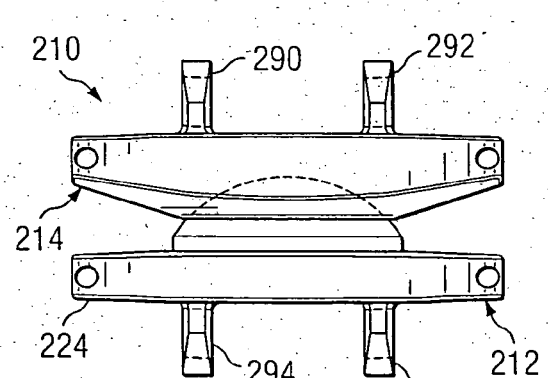
FIG. 19 is a longitudinal view of an alternative articulating prosthetic joint for anterior insertion according to yet another embodiment of the present disclosure.
Figure 20:
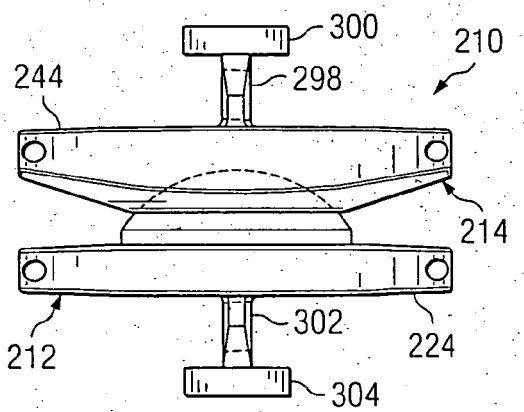
FIG. 20 is a longitudinal view of an alternative articulating prosthetic joint for anterior insertion according to yet another embodiment of the present disclosure.

Referring now to FIGS. 18-20, in other embodiments, one or both of the articular components 212, 214 may include different numbers of keels and/or modified keels. Referring specifically to FIG. 18, two keels, designated 290 and 292, extend from the bearing surface 244 and are configured for disposition within preformed openings in the adjacent vertebral endplate. In one embodiment, both keels 290, 292 extend perpendicularly from the bearing surface 244 and are parallel and equally spaced along a central portion of the bearing surface 244.

Referring specifically to FIG. 19, two keels, designated 294 and 296, extend from the bearing surface 224 and are configured for disposition within preformed openings in the adjacent vertebral endplate. In one embodiment, both keels 294, 296 extend perpendicularly from the bearing surface 224 and are parallel and equally spaced along a central portion of the bearing surface 224. It should be understood that other positions and orientations of the keels 290, 292, 294, and 296 are also contemplated.

Referring specifically to FIG. 20, a keel 298 extends from the bearing surface 244 similar to the keel 260 of FIG. 14, except that the keel 298 includes a laterally-extending or "winged" portion 300 opposing the bearing surface 244. The winged portion 300 can provide several functions, including maintaining the bearing surface 244 tightly against the body $V_U$, and substantially preventing any longitudinal movement of the articular component 214. Similarly, a keel 302 extends from the bearing surface 224 and includes a winged portion 304 opposing the bearing surface 224. The winged portion 304 can provide several functions, including maintaining the bearing surface 224 tightly against the body $V_L$, and substantially preventing any longitudinal movement of the articular component 212.

Figure 21:
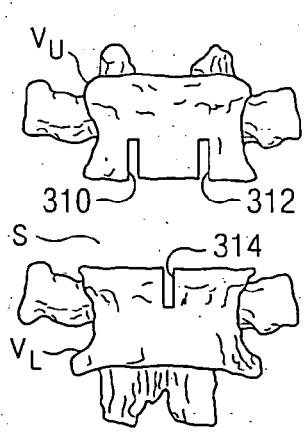
FIG. 21 is a longitudinal view of a pair of verterbral endplates having slots for receiving the prosthetic joint of FIG. 18.
Figure 22:
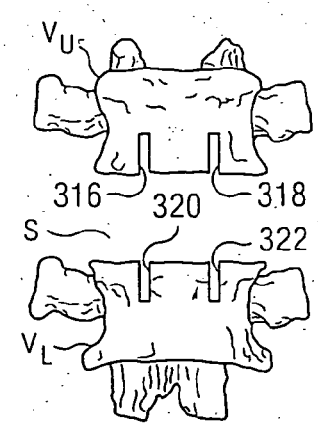
FIG. 22 is a longitudinal view of a pair of verterbral endplates having slots for receiving the prosthetic joint of FIG. 19.
Figure 23:
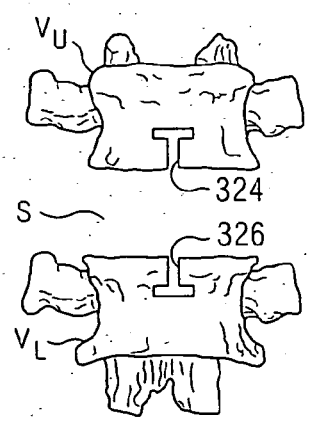
FIG. 23 is a longitudinal view of a pair of verterbral endplates having slots for receiving the prosthetic joint of FIG. 20.

Referring to FIGS. 21-23, to accommodate insertion of the above-described alternative prosthetic joints 210 within the intervertebral space S, the upper and lower vertebrae $V_U$, $V_L$ can be prepared to accept each of the articulating joints 210 therebetween. Referring specifically to FIG. 21, for the configuration of the prosthetic joint 210 of FIG. 18, multiple slots 310 and 312 are formed along the vertebral endplate of the upper vertebrae $V_U$, and a single slot 314 is formed along the vertebral endplate of the lower vertebrae $V_L$. Referring specifically to FIG. 22, for the configuration of the prosthetic joint 210 of FIG. 19, multiple slots 316, 318 and 320, 322 are formed along the vertebral endplates of the upper vertebrae $V_U$, and lower vertebrae $V_L$, respectively. Referring specifically to FIG. 23, for the configuration of the prosthetic joint 210 of FIG. 20, winged slots 324, 326 are formed along the vertebral endplates of the upper vertebrae $V_U$ and the lower vertebrae $V_L$, respectively. The preparation of the slots 310, 312, 314, 316, 318, 320, 322, 324, 326 can be accomplished in a similar manner to those discussed above with respect to FIG. 17. For the winged slots 324, 326, a standard chisel can be used, or alternatively, a unique wing-shaped chisel can be used.

Figure 24:
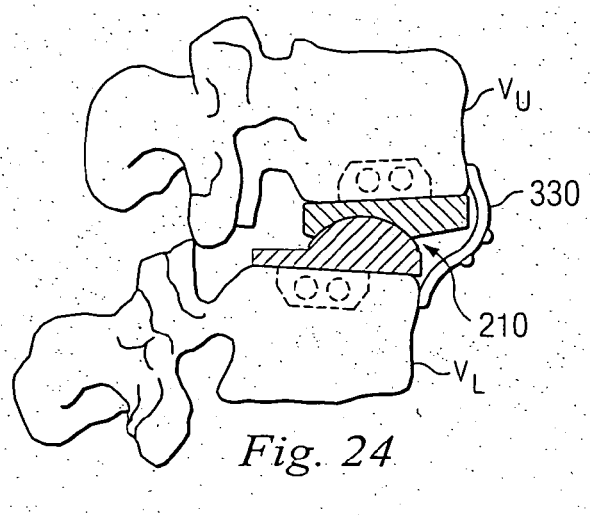
FIG. 24 is a lateral, partial sectional view of the prosthetic joint of FIG. 14 disposed between a pair of spondylosed vertebral endplates and an orthopedic implant.

Referring to FIG. 24, in addition to the prosthetic joint 210, a woven orthopedic implant 330 can be used to act as an artificial ligament between the two vertebrae $V_U$, $V_L$. One embodiment of the woven implant 330 is disclosed in U.S. Ser. No. 10/082,579, which is incorporated by reference. The implant 330 functions as a natural ligament would function, and helps to stabilize and further secure the two vertebrae $V_U$, $V_L$ together, and helps to discourage further displacement (or prevent the displacement from returning to the way it was pre-surgery).

Figure 25:
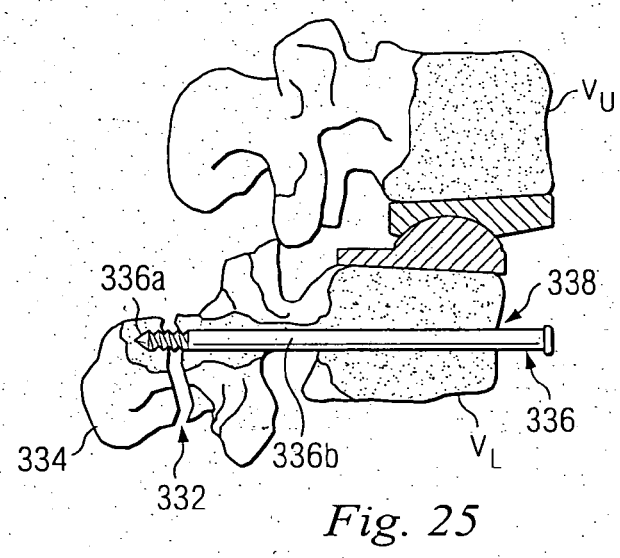
FIG. 25 is a lateral, partial sectional view of the prosthetic joint of FIG. 14 disposed between a pair of spondylosed vertebral endplates and a lag screw.
Figure 26:
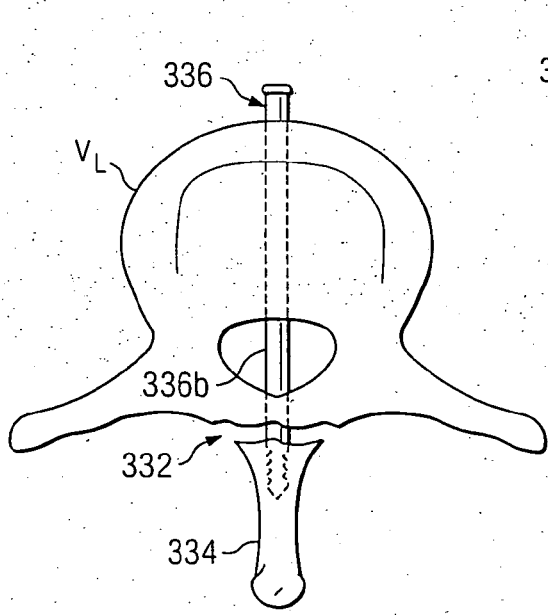
FIG. 26 is a schematic top view of the arrangement depicted in FIG. 25.

Referring to FIGS. 25 and 26, it is contemplated that a pars fracture, such as is illustrated by a fracture in a bony element 332 that connects a posterior element, such as an articular process 334 to the vertebra $V_L$, may also be treated during correction of spondylolisthesis from the anterior approach. It is understood that the fractured bony element 332 is exaggerated in the FIG. 25 for the sake of improved clarity. The pars fracture can be repaired by driving a lag screw 336 having a threaded portion 336a and a non-threaded portion 336b into an opening 338 in the vertebral body $V_L$, through the bony element 332, and into the articular process 334. In some embodiments, all or part of the opening 338 can be pre-drilled with a drill or chisel (not shown). The lag screw 336 is inserted and accessed through the anterior direction, and multiple screws can be used to repair multiple processes. By capturing the fractured posterior element and tightening the lag screw 336, the vertebrae $V_L$ is repaired.

III. Transforaminal Prosthetic Joint

In some instances, it is often difficult to approach and clear a defective intervertebral disc space due to potential damage to important anatomical structures such as nerve roots, dura, ligamentum flavum and interspinous ligament. For example, preservation of the ligamentous structures is of great importance to restore biomechanical stability of the segment and its adjacent counterparts. In these situations, a transforaminal approach may allow clearance of the entire intervertebral disc space by opening the neuroforamen on one side. After appropriate clearance, it is possible to achieve further enlargement of the cleared intervertebral compartment by posterior transpedicle distraction. While this approach has been used for fusion techniques, such as Transforaminal Lumbar Interbody Fusion, or TLIF, it has not heretofore been used with motion preserving implants.

Figure 27:
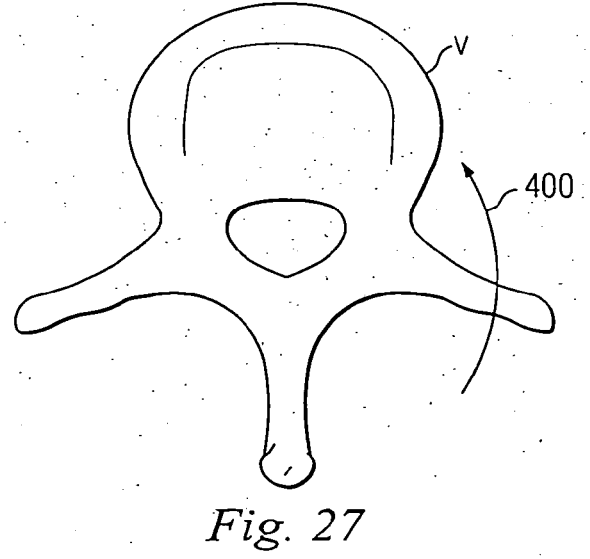
FIG. 27 is a schematic top view of a vertebral body depicting a path for transforaminal insertion.

Referring to FIG. 27, in a transforaminal approach, the disc V is approached as shown by the arrow 400. The approach is between a posterior approach and a lateral approach, and in some cases, only one side of the disc needs to be exposed (right or left) in order to perform the procedure.

Figure 28:
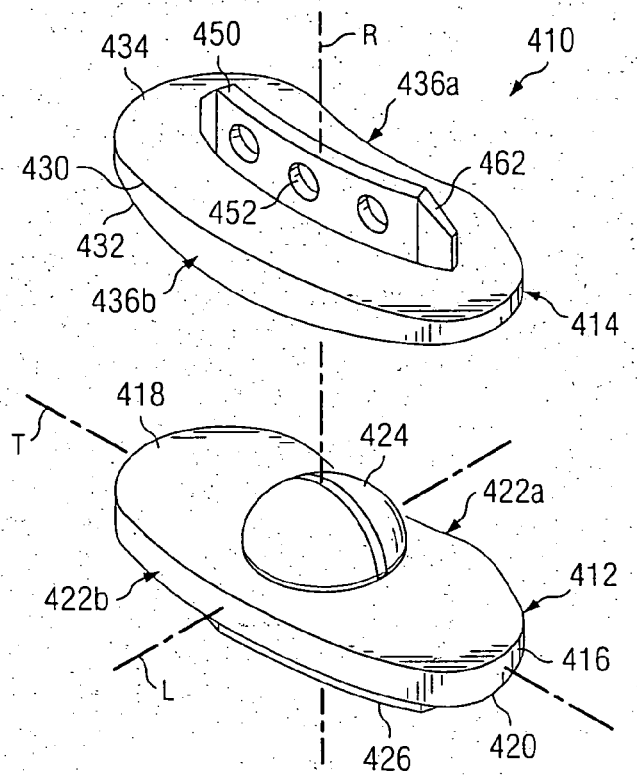
FIG. 28 is an isometric view of an alternative articulating prosthetic joint for transforaminal insertion according to another embodiment of the present disclosure.
Figure 29:
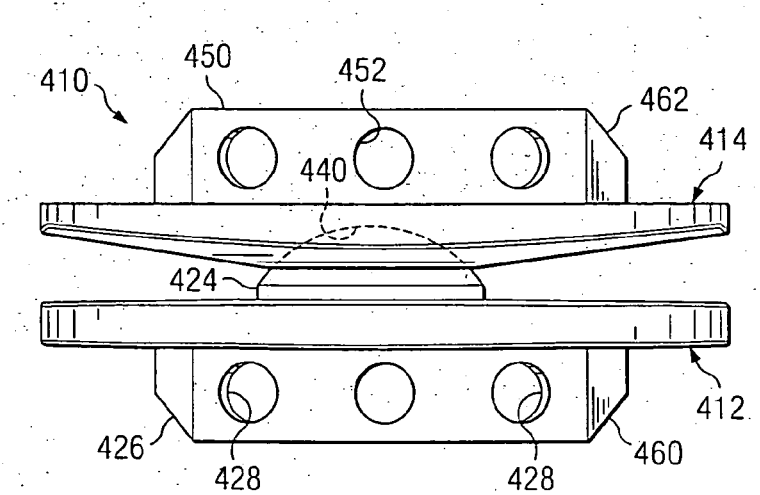
FIG. 29 is a lateral view of the prosthetic joint of FIG. 28.
Figure 30:
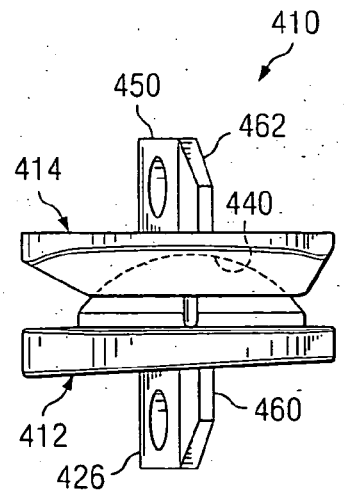
FIG. 30 is a longitudinal view of the prosthetic joint of FIG. 28.

Referring to FIGS. 28-30, shown therein is an intervertebral articulating prosthetic joint 410 according to another form of the present disclosure. The articulating joint 410 extends generally along a longitudinal axis L and includes a first articular component 412 and a second articular component 414. The articular components 412, 414 cooperate to form the articulating joint 410 which is sized and configured for disposition within an intervertebral space between adjacent vertebral bodies.

The prosthetic joint 410 provides relative pivotal and rotational movement between the adjacent vertebral bodies to maintain or restore motion substantially similar to the normal bio-mechanical motion provided by a natural intervertebral disc. More specifically, the articular components 412, 414 are permitted to pivot relative to one another about a number of axes, including lateral or side-to-side pivotal movement about longitudinal axis L and anterior-posterior pivotal movement about a transverse axis T. It should be understood that in one embodiment, the articular components 412, 414 are permitted to pivot relative to one another about any axes that lies in a plane that intersects longitudinal axis L and transverse axis T. Additionally, the articular components 412, 414 are preferably permitted to rotate relative to one another about a rotational axis R. Although the articulating joint 410 has been illustrated and described as providing a specific combination of articulating motion, it should be understood that other combinations of articulating movement are also possible and are contemplated as falling within the scope of the present disclosure. It should also be understood that other types of articulating movement are also contemplated, such as, for example, relative translational or linear motion.

Although the articular components 412, 414 of prosthetic joint 410 may be formed from a wide variety of materials, in one embodiment, the articular components 412, 414 are formed of a cobalt-chrome-molybdenum metallic alloy (ASTM F-799 or F-75). However, in alternative embodiments, the articular components 412, 414 may be formed of other materials such as titanium or stainless steel, a polymeric material such as polyethylene, or any other biocompatible material that would be apparent to one of ordinary skill in the art. The surfaces of the articular components 412, 414 that are positioned in direct contact with vertebral bone are preferably coated with a bone-growth promoting substance, such as, for example, a hydroxyapatite coating formed of calcium phosphate. Additionally, the surface of the articular components 412, 414 that are positioned in direct contact with vertebral bone are preferably roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

Articular component 412 includes a support plate 416 having an articular surface 418 and an opposite bearing surface 420. Support plate 416 may be sized and shaped to substantially correspond to the size and shape of the vertebral endplate of an adjacent vertebra. In one embodiment, the support plate 416 is shaped to facilitate a transforaminal insertion approach. As such, the support plate 416 includes curved side portions 422a, 422b, which are defined as the generally elongated portions of the support plate 416 extending between articular surface 418 and the bearing surface 420. Although not shown, the support plate 416 can include one or more notches or other types of indicia for receiving and engaging with a corresponding portion of a surgical instrument (also not shown) to aid in the manipulation and insertion of the prosthetic joint 410 within an intervertebral space between adjacent vertebrae. The surgical instrument (not shown) is preferably configured to hold the articular components 412, 414 at a predetermined orientation and spatial relationship relative to one another during manipulation and insertion of the prosthetic joint 410, and to release the articular components 412, 414 once properly positioned between the adjacent vertebrae.

In one embodiment, the articular surface 418 includes a projection 424 having a convex shape, which may be configured as a spherical-shaped ball (half of which is shown). It should be understood that other configurations of the projection 424 are also contemplated, such as, for example, cylindrical, elliptical or other arcuate configurations or possibly non-arcuate configurations. It should also be understood that the remaining portion of articular surface 418 may take on planar or non-planar configurations, such as, for example, an angular or conical configuration extending about the projection 424.

A flange member or keel 426 extends from the bearing surface 410 and is configured for disposition within a pre-formed opening in the adjacent vertebral endplate. In one embodiment, the keel 426 extends perpendicularly from the bearing surface 420 and is approximately centrally located along the bearing surface 420. However, it should be understood that other positions and orientations of the keel 426 are also contemplated.

In one embodiment, the keel 426 transversely extends along a substantial portion of the support plate 416. The keel 426 is curved, generally in a direction similar to the arrow 400 of FIG. 27. The degree of curvature of the keel 426 may be substantially similar to and congruous with the degree of curvature of the side portions 422a, 422b. Such an embodiment would accommodate insertion of the prosthetic joint 410 using a transforaminal approach as opposed to the anterior or lateral approaches discussed above. In a further embodiment, the keel 426 may be angled, tapered, or configured in some other shape to facilitate the functional demands of the keel. In still another embodiment, the keel 426 may be configured as a winged keel, including a transverse portion (not shown) extending across the main body portion of keel 426.

The keel 426 also includes three openings 428 extending therethrough to facilitate bone through-growth to enhance fixation to the adjacent vertebra. However, it should be understood that any number of openings 428 may be defined through keel 426, including a single opening or three or more openings. It should also be understood that the openings 428 need not necessarily extend entirely through the keel 426, but may alternatively extend partially therethrough. It should further be understood that the keel 426 need not necessarily define any openings 428 extending either partially or entirely therethrough. Additionally, although the openings 428 are illustrated as having a circular configuration, it should be understood that other sizes and configurations of openings 428 are also contemplated. As discussed above, the surfaces of the articular component 412 that are in direct contact with vertebral bone are preferably coated with a bone-growth promoting substance. Specifically, the bearing surface 420 and the surfaces of the keel 426 can be coated with hydroxyapatite to promote bony engagement with the adjacent vertebrae. As also discussed above, the bearing surface 420 and the surfaces of keel 426 can be roughened prior to application of the hydroxyapatite coating.

In one embodiment, the articular component 414 includes a support plate 430 having an articular surface 432 and an opposite bearing surface 434. Support plate 430 may be sized and shaped to substantially correspond to the size and shape of the vertebral endplate of an adjacent vertebra. In one embodiment, the support plate 430 is shaped to facilitate a transforaminal insertion approach. As such, the support plate 416 includes curved side portions 436a, 436b, which are defined as the generally elongated portions of the support plate 430 extending between articular surface 432 and the bearing surface 434. Although not shown, the support plate 430 can include one or more notches or other types of indicia for receiving and engaging with a corresponding portion of a surgical instrument, such as discussed above with reference to articular element 412.

In one embodiment, the articular surface 432 includes a recess 440 having a concave shape, which may be configured as a spherical-shaped socket. However, it should be understood that other configurations of the recess 440 are also contemplated, such as, for example, cylindrical, elliptical or other arcuate configurations or possibly non-arcuate configurations. The remaining portion of the articular surface 432 can be angled or otherwise configured to facilitate the insertion and/or use of the prosthesis.

Although the concave recess 440 is illustrated as having a generally smooth, uninterrupted articular surface, it should be understood that a surface depression or cavity may be defined along a portion of the recess 440 to provide a means for clearing out matter, such as particulate debris, that is disposed between the abutting articular surfaces of components 412, 414. In such case, the convex articular surface of the ball 424 may alternatively define a generally smooth, uninterrupted articular surface. In another embodiment, each of the convex projection 424 and the concave recess 440 may define a surface depression to facilitate removal of particulate matter disposed between the abutting articular surfaces.

A flange member or keel 450, configured similar to the keel 426 of articular component 412, extends from the bearing surface 434. In one embodiment, the keel 450 can be centrally located, and is positioned directly or parallel in-line with the keel 450. The keel 450 is curved, in a direction similar to the keel 426 and the arrow 400 of FIG. 27. The degree of curvature of the keel 450 may be substantially similar to and congruous with the degree of curvature of the side portions 436a, 436b. Such an embodiment would accommodate insertion of the prosthetic joint 410 using a transforaminal approach as opposed to the anterior or lateral approaches discussed above. In some embodiments, the position of the keel 450 can be offset to help circumvent veins, arteries, bony portions, or other obstacles that may be in place during the insertion of the joint 410.

It should also be understood that the keel 450 may also be differently positioned, shaped or oriented, or more keels 450 can be used, for similar or additional reasons. Also, the keel 450 may be angled, tapered, or configured in some other shape to facilitate the functional demands of the keel. In still another embodiment, the keel 450 may be configured as a winged keel, including a transverse portion (not shown) extending across the main body portion of keel 450.

In one embodiment, the keel 450 also includes three openings 452 extending therethrough to facilitate bone through-growth to enhance fixation to the adjacent vertebra. However, it should be understood that any number of openings 452 may be defined through keel 450, including a single opening or three or more openings. It should also be understood that the openings 452 need not necessarily extend entirely through the keel 450, but may alternatively extend partially therethrough. It should further be understood that the keel 450 need not necessarily define any openings 452 extending either partially or entirely therethrough. Additionally, although the openings 452 are illustrated as having a circular configuration, it should be understood that other sizes and configurations of openings 452 are also contemplated. As discussed above, the surfaces of the articular component 414 that are in direct contact with vertebral bone are preferably coated with a bone-growth promoting substance. Specifically, the bearing surface 434 and the surfaces of the keel 450 can be coated with hydroxyapatite to promote bony engagement with the adjacent vertebrae. As also discussed above, the bearing surface 434 and the surfaces of keel 450 can be roughened prior to application of the hydroxyapatite coating.

In some embodiments, one or both of the keels 426, 450 may include a sharp forward edge, illustrated by edges 460, 462, respectively, of FIG. 28c. By having such an edge, insertion of the keel into the associated vertebral body is facilitated. Also, the edges 460, 462 can be of sufficient sharpness that the vertebral bodies do not require a slot for receiving the keels 426, 450, discussed in greater detail below.

Figure 31A:
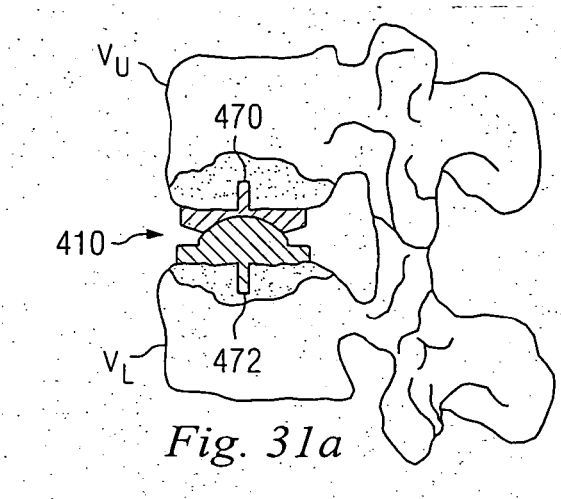
FIG. 31a is a lateral, partial sectional view of the prosthetic joint of FIG. 28 disposed between a pair of vertebral endplates.
Figure 31B:
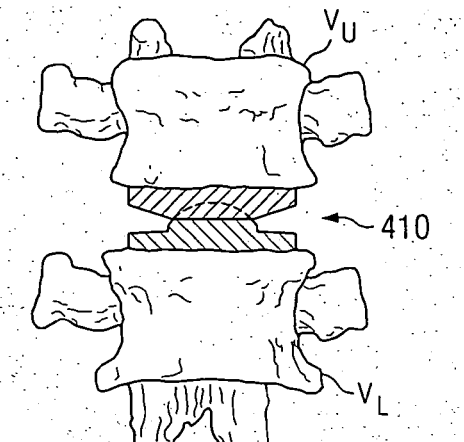
FIG. 31b is a longitudinal, partial sectional view of the prosthetic joint of FIG. 28 disposed between a pair of vertebral endplates.

Referring to FIGS. 31a and 31b, to accommodate insertion of the prosthetic joint 410 within the intervertebral space, the upper and lower vertebrae $V_U$, $V_L$ can be prepared to accept the prosthetic joint 410 therebetween. Referring specifically to FIG. 31a, for the configuration of the prosthetic joint 410 of FIGS. 28-30, multiple slots 470, 472 are formed along the vertebral endplates of the upper vertebrae $V_U$ and the lower vertebrae $V_L$. The slots 470, 472 can be created by the keels 426, 450 themselves, or can be prepared beforehand.

Figure 32:
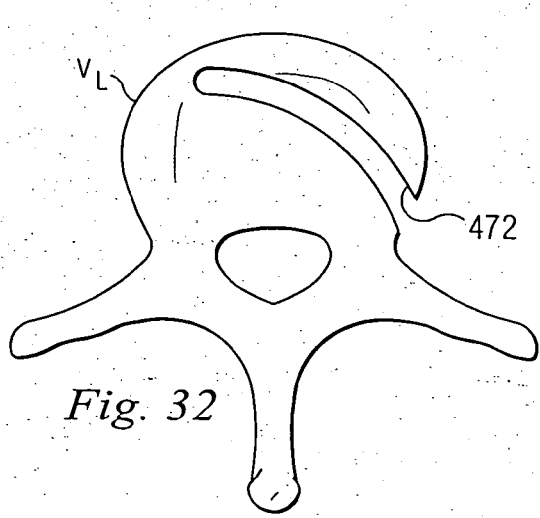
FIG. 32 is a schematic top view depicting a transforaminal slot formed in a vertebral endplate.

Referring also to FIG. 32, it may be desirable to prepare one or more of the slots 470, 472 before the prosthetic joint 410 is inserted between the upper and lower vertebrae $V_U$, $V_L$. The slots 470, 472 can be curved, as illustrated by the slot 472, in accordance with the curved keels 426, 450, to facilitate the movement of the prosthetic joint 410 during insertion.

Figure 33:
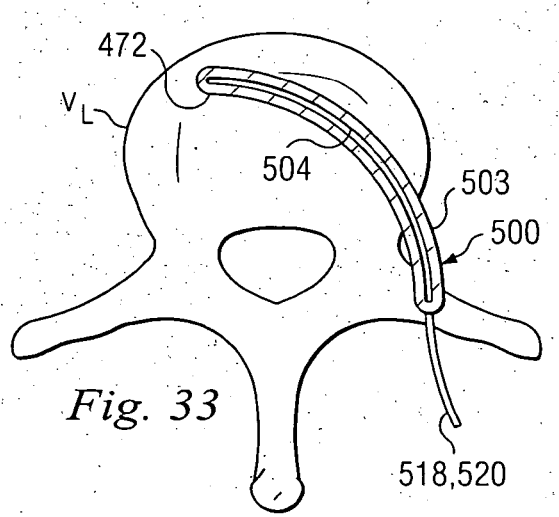
FIG. 33 is a schematic top view depicting a milling apparatus shown inserted above a vertebral endplate.
Figure 34A:
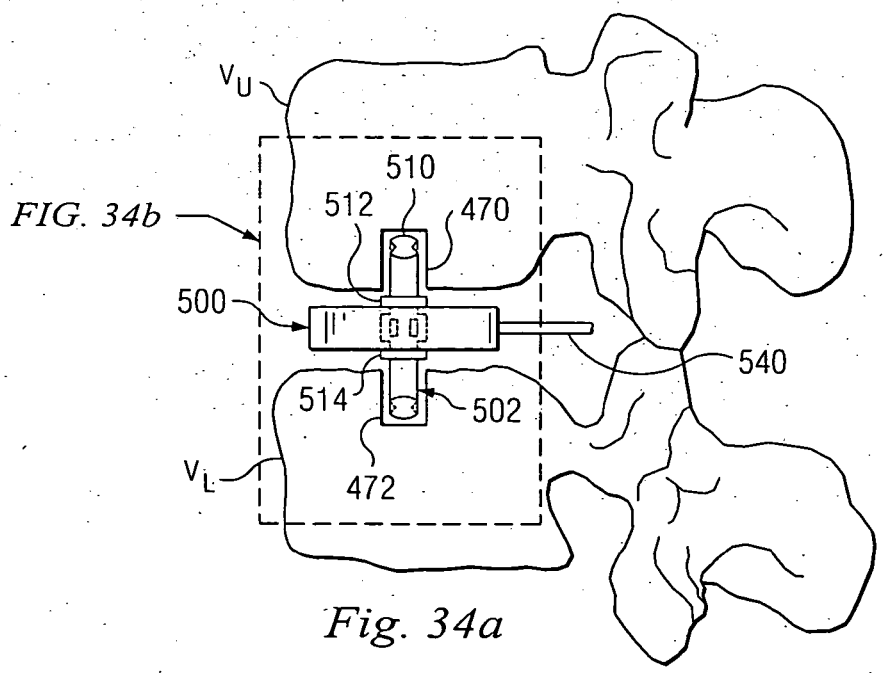
FIG. 34a is a lateral view of the milling apparatus of FIG. 33 shown disposed between a pair of adjacent vertebral endplates.
Figure 34B:
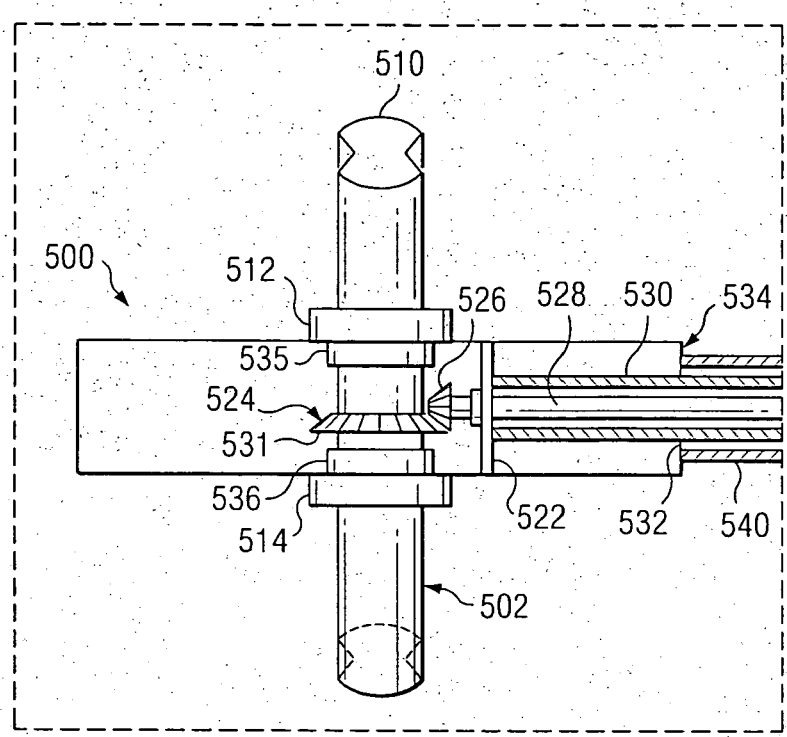
Figure 34C:
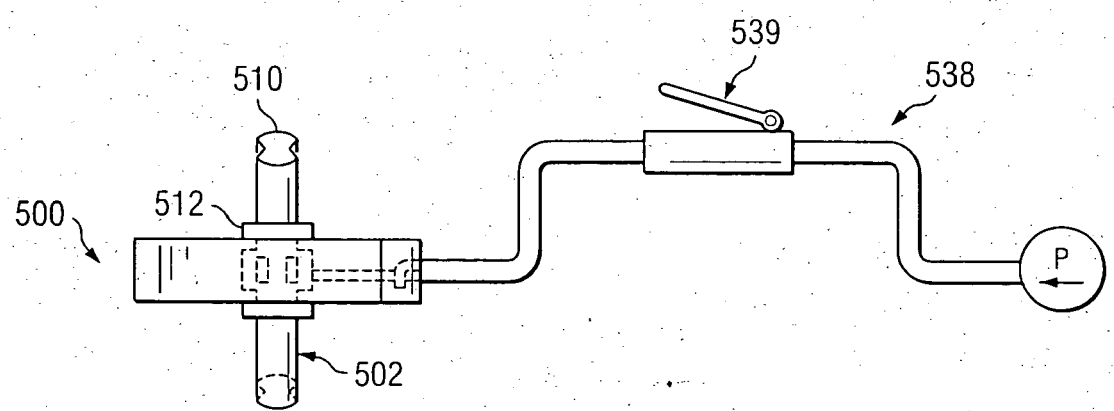
FIG. 34c is a detailed view of an alternative milling tool.
Figure 35:
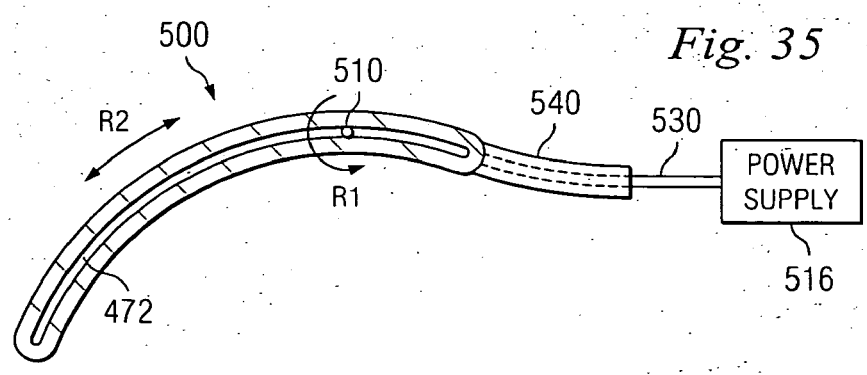
FIG. 35 is a schematic view of the milling apparatus of FIG. 33.

Referring to FIGS. 33-35, as an alternative to chiseling, which provides only for the cutting of straight slots, a milling guide 500 may be used in conjunction with a milling tool 502 to cut the curved slots 470, 472 (represented by 472 in FIG. 32) in the upper and lower vertebral bone $V_U$, $V_L$. The milling guide 500 and milling tool 502 may be formed of any material including biocompatible materials such as titanium. The milling guide 500 includes an elongated curved member 503, which defines a curved opening 504 to correspond to the shape of the desired curve for the slots 470, 472. Of course, the degree of curvature of the milling guide 500, and therefore the curved opening 504, may vary depending on the desired curve of the slots 470, 472. In one embodiment, the milling guide 500 is formed of a pliable material that retains a rigid shape upon reforming such that the degree of curvature of the curved opening 504 may be altered without having to swap out milling guides. The milling guide 500, and therefore the curved opening 504, is also of sufficient length so that if the slots 470, 472 need to be continued through any posterior elements of the vertebrae, such extension of the slots can be accomplished at the same time.

Referring specifically to FIGS. 34a and 34b, in one embodiment, the milling tool 502 includes a milling bit 510 that is positioned to be rotated and translated in the curved opening 504. In one embodiment, the milling bit 510 is a double fluted routing bit, that may extend simultaneously into the upper and lower vertebrae $V_U$, $V_L$.

The milling bit 510 is also adapted to receive a translational force such that the milling bit can be moved back and forth in the curved opening 504. Referring to FIG. 34b, in one embodiment, a milling bit handle 530 is connected in any conventional manner to a housing 522 (a portion of which is shown). The handle 530 extends from the housing 522 and through a slot 532 formed in a proximal end 534 of the milling guide 500 relative to a surgeon (not depicted). As such, the handle 530 can be translated by a surgeon, thereby translating the milling bit 510 through the curved opening 504. In this manner, the handle 530 is adapted to impart translational movement to the milling bit 510. To accommodate movement of the milling bit 510 within the curved opening 504, a pair of bearing assemblies 512, 514 may be positioned adjacent to the housing 522 to guide the milling bit 510 along the curved opening.

The housing 522 houses a rotation assembly, which, in one embodiment, is a gear assembly 524. The gear assembly 524 includes a drive gear 526 connected to and extending annularly around a rotatable shaft 528. The shaft 528 is rotatable via an external source represented by power supply 516 (FIG. 35). In one embodiment, the shaft 528 is housed within the handle 530.

The gear assembly 524 further includes a bit gear 530, which is connected to and extends annularly around the milling bit 510. The bit gear 530 is positioned on the milling bit 510 such that the bit gear is orthogonal relative to and in contact with the drive gear 526. Thus, rotation of the shaft 528 imparts rotation to the milling bit 510 via the gear assembly 524. A pair of annular shoulders 534, 536 are also connected to the milling bit 510 such that the milling bit can easily move back and forth through the curved opening 504 without slippage in the upper or lower directions as viewed in FIG. 34b. It is understood that the gear assembly 524 is merely exemplary of an assembly that may be used to impart rotational motion to the milling bit 510. Other types of rotation-imparting assemblies are contemplated as falling within the present disclosure such as pneumatic-type systems.

Referring to FIG. 34c, in one such embodiment, a pneumatic system 538 may be employed to impart rotation to the milling bit 510. In one embodiment, a Medtronic Midas Rex® Legend™ motor is used to supply power (represented by P) to the pneumatic system. A conventional valve 539 is used to control the air flow and pressure supplied to rotate the milling bit 510. In still other embodiments, manual or combination power supplies are contemplated as being the preferred power supply 516 (FIG. 34b) and P (FIG. 34c).

Referring again to FIGS. 34a and 34b, a guide handle 540 is further provided such that the milling guide 500 is independently movable relative to the milling bit 510. Thus in one embodiment, the milling guide 500 can be held via the guide handle 540 with one hand while the milling bit 510 may be moved within the curved opening 504 via the handle 530 with the other hand. In some embodiments, the handle 530 may extend through the guide handle 540 as shown in FIG. 34b. As a result, and referring to FIG. 35, the milling bit 510 is adapted to rotate in a direction indicated by arrow R1, and is adapted to be translated through the curved opening 504 in the directions indicated by arrow R2.

In operation, the milling guide 500 and the milling tool 502 can be used to cut a slot, such as the slot 472, to prepare the vertebral body $V_L$ to receive the lower portion of the prosthetic joint 410. The surgeon first selects the desired amount of curvature to impart to the slot 472 and selects or configures the corresponding milling guide 500. The surgeon then approaches the vertebral body $V_L$ from the transforaminal approach to position the milling guide 500 into the disc space between the upper and lower vertebrae $V_U$, $V_L$ and to abut the milling bit 510 against the upper and lower vertebrae $V_U$, $V_L$. Upon proper positioning, the surgeon may then actuate the milling tool 502 via the power supply 516 to begin cutting into the upper and lower vertebrae $V_U$, $V_L$ with the milling bit 510.

The milling guide 500 may be held by the surgeon or via an external instrument such that the milling guide is stationary during translational movement of the milling bit 510 through the milling guide. The curvature of the milling guide 500 guides the milling bit 510 transforaminally through the upper and lower vertebrae $V_U$, $V_L$ to cut a transforaminal slot, such as the slot 472 depicted in the lower vertebra $V_L$ FIG. 32, to prepare the upper and lower vertebrae to receive the transforaminal prosthetic joint 410.

Figure 37:
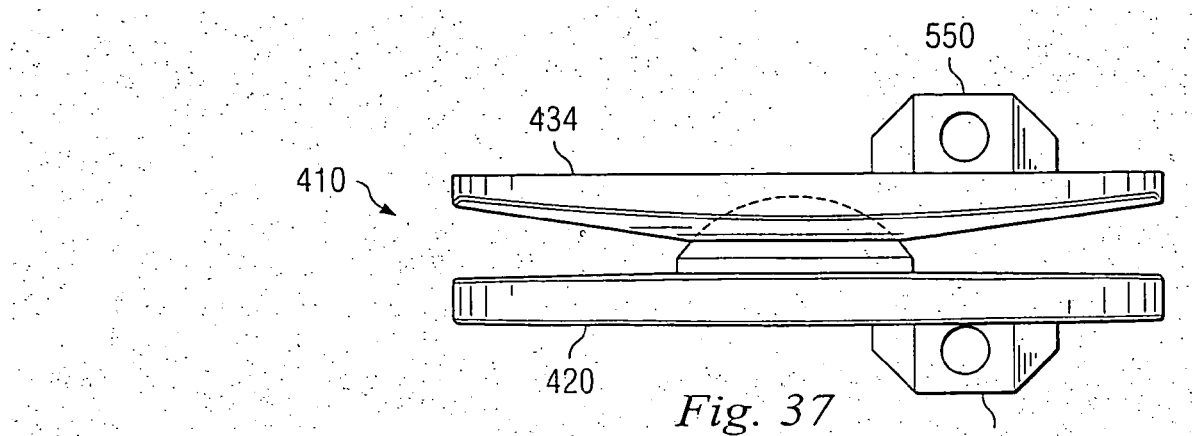
FIG. 37 is a lateral view of the prosthetic joint of FIG. 36.
Figure 36:
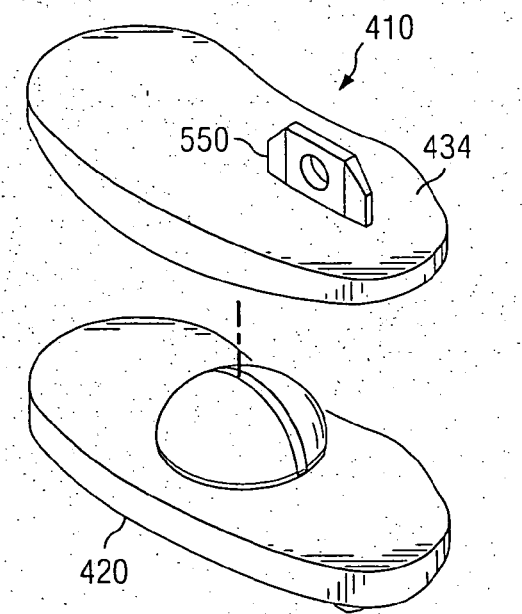
FIG. 36 is an isometric view of an alternative articulating prosthetic joint for transforaminal insertion according to another embodiment of the present disclosure.
Figure 38:
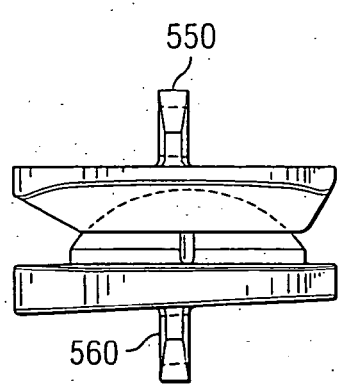
FIG. 38 is a longitudinal view of the prosthetic joint FIG. 36.

In an alternative embodiment, the keels of the prosthetic joint 410 may take alternative shapes and configurations to assist in the curved, transforaminal approach used in inserting the joint. Referring to FIGS. 36-38, the keels, designated 550 and 560, extend from the bearing surfaces 434 and 420, respectively. The keels 550, 560 are relatively short and thus extend along a short portion of the bearing surfaces 434, 420, respectively, in comparison to the keels 450, 426 of FIGS. 28-30. The relative shortness of the keels 550, 560 may aid such keels in following the openings 470, 472, respectively. In addition, the shortness of the keels 550, 560 and the ease with which such keels follow the openings 470, 472, respectively, allows the keels to be configured as either straight or curved keels, which increases the design options of the prosthetic joint 410. The keels 550, 560 may also be tapered to assist in insertion of the keels into the upper and lower vertebrae $V_U$, $V_L$.

IV. Anterior-Oblique Prosthetic Joint

Another approach that can be used to avoid potential damage to important anatomical structures such as nerve roots, dura, ligamentum flavum and interspinous ligament is the anterior oblique approach. For example, the straight anterior approach to the disc space between vertebra L4 and L5, as well as the superior disc levels, can present high surgical risks during the insertion of a total disc replacement implant because of the attachment of the major vessels to the anterior aspect of the spine.

Figure 39:
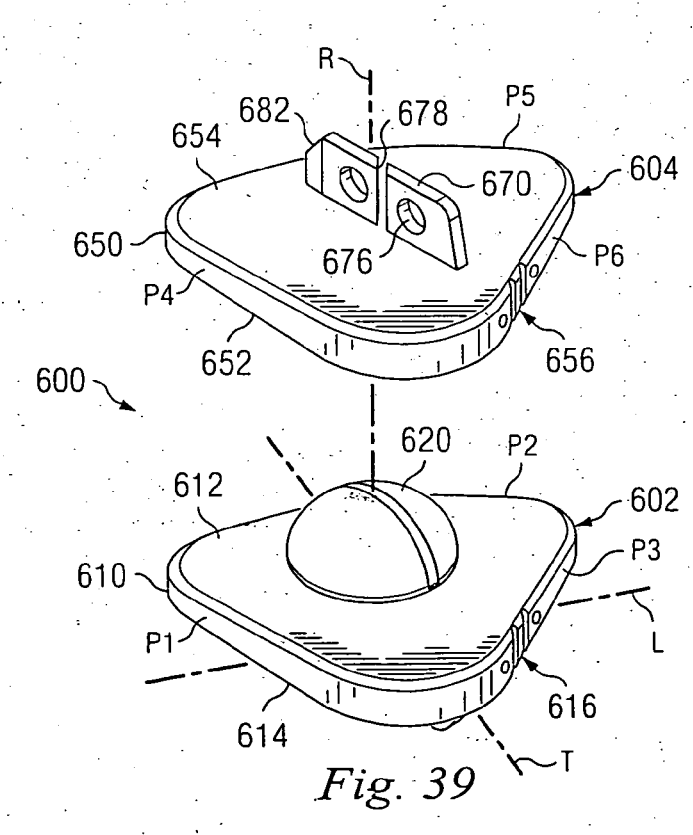
FIG. 39 is an isometric view of an alternative articulating prosthetic joint for anterior-oblique insertion according to another embodiment of the present disclosure.
Figure 40:
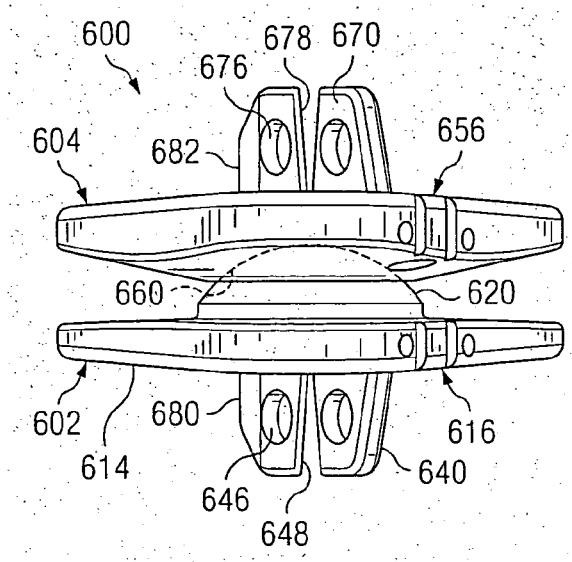
FIG. 40 is a longitudinal view of the prosthetic joint of FIG. 39.
Figure 41:
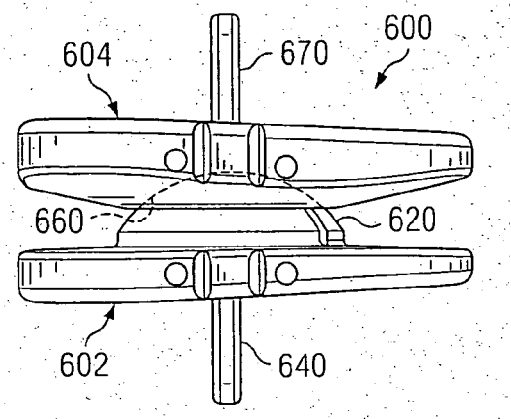
FIG. 41 is a lateral view of the prosthetic joint of FIG. 39.
Figure 42:
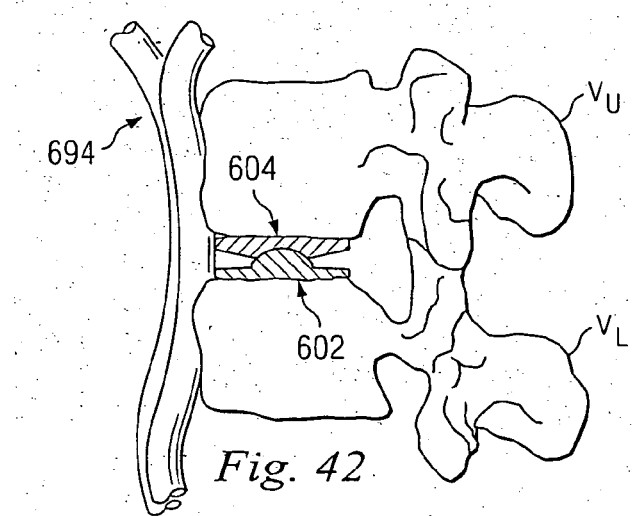
FIG. 42 is lateral, partial sectional view of the prosthetic joint of FIG. 39 disposed between a pair of vertebral endplates.

Referring to FIGS. 39-41, shown therein is an intervertebral articulating prosthetic joint 600 according to another form of the present disclosure. The prosthetic joint 600 extends generally along a longitudinal axis L and includes a first articular component 602 and a second articular component 604. The articular components 602, 604 cooperate to form the prosthetic joint 600 which is sized and configured for disposition within an intervertebral space between adjacent vertebral bodies.

The prosthetic joint 600 provides relative pivotal and rotational movement between the adjacent vertebral bodies to maintain or restore motion substantially similar to the normal bio-mechanical motion provided by a natural intervertebral disc. More specifically, the articular components 602, 604 are permitted to pivot relative to one another about a number of axes, including lateral or side-to-side pivotal movement about longitudinal axis L and anterior-posterior pivotal movement about a transverse axis T. It should be understood that in a preferred embodiment, the articular components 602, 604 are permitted to pivot relative to one another about any axes that lies in a plane that intersects longitudinal axis L and transverse axis T. Additionally, the articular components 602, 604 may be permitted to rotate relative to one another about a rotational axis R. Although the articulating joint 600 has been illustrated and described as providing a specific combination of articulating motion, it should be understood that other combinations of articulating movement are also possible and are contemplated as falling within the scope of the present disclosure. It should also be understood that other types of articulating movement are also contemplated, such as, for example, relative translational or linear motion.

Although the articular components 602, 604 of prosthetic joint 600 may be formed from a wide variety of materials, in one embodiment, the articular components 602, 604 are formed of a cobalt-chrome-molybdenum metallic alloy (ASTM F-799 or F-75). However, in alternative embodiments of the invention, the articular components 602, 604 may be formed of other materials such as titanium or stainless steel, a polymeric material such as polyethylene, or any other biocompatible material that would be apparent to one of ordinary skill in the art. The surfaces of the articular components 602, 604 that are positioned in direct contact with vertebral bone are preferably coated with a bone-growth promoting substance, such as, for example, a hydroxyapatite coating formed of calcium phosphate. Additionally, the surface of the articular components 602, 604 that are positioned in direct contact with vertebral bone are preferably roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

Articular component 602 includes a support plate 160 having an articular surface 612 and an opposite bearing surface 614. Support plate 610 may be sized and shaped to substantially correspond to the size and shape of the vertebral endplate of an adjacent vertebra. In one embodiment, the support plate 610 is shaped in a triangular-like configuration to facilitate an oblique insertion approach from either the left or right side of the spine, and as such, includes side portions P1, P2 and P3. The side portions P1, P2 and P3 may take a variety of configurations including curved (illustrated by P2) or straight (illustrated by P1 and P3) configurations.

The support plate 610 can include one or more notches 616 or other types of indicia for receiving and engaging with a corresponding portion of a surgical instrument (also not shown) to aid in the manipulation and insertion of the prosthetic joint 600 within an intervertebral space between adjacent vertebrae. The surgical instrument (not shown) is preferably configured to hold the articular components 602, 604 at a predetermined orientation and spatial relationship relative to one another during manipulation and insertion of the prosthetic joint 600, and to release the articular components 602, 604 once properly positioned between the adjacent vertebrae.

In one embodiment, the articular surface 612 includes a projection 620 having a convex shape, which may be configured as a spherical-shaped ball (half of which is shown). It should be understood that other configurations of the projection 620 are also contemplated, such as, for example, cylindrical, elliptical or other arcuate configurations or possibly non-arcuate configurations. It should also be understood that the remaining portion of articular surface 612 may take on planar or non-planar configurations, such as, for example, an angular or conical configuration extending about the projection 620.

A flange member or keel 640 extends from the bearing surface 614 and is configured for disposition within a preformed opening in the adjacent vertebral endplate. In one embodiment, the keel 640 extends perpendicularly from the bearing surface 614 and is approximately centrally located along the bearing surface 614. However, it should be understood that other positions and orientations of the keel 640 are also contemplated. Furthermore, more keels 640 can be used, for similar or additional reasons.

In one embodiment, the keel 640 extends along a substantial portion of the support plate 610. The keel 640 is straight, but extends along a direction towards the notches 616 and is parallel with one of the side portions P1 of the support plate 610. In the present example, the keel 640 is positioned between the transverse axis T and lateral axis L. Such an embodiment accommodates insertion of the prosthetic joint 600 using an oblique approach as opposed to the anterior, lateral, or transforaminal approaches discussed above. In a further embodiment, the keel 640 may be angled, tapered, or configured in some other shape to facilitate the functional demands of the keel. In still another embodiment, the keel 640 may be configured as a winged keel, including a transverse portion (not shown) extending across the main body portion of keel 640.

The keel 640 also includes a pair of openings 646 extending therethrough to facilitate bone through-growth to enhance fixation to the adjacent vertebra. Additionally, a gap 648 may also be formed in the keel 640 to further facilitate bone through-growth. The gap 648 also provides a reference point such that an X-ray can be used to evaluate the positioning and alignment of the support plate 602 during insertion of the prosthetic joint 600. It should be understood that any number of openings 646 or gaps 648 may be defined through keel 640, including a single opening or gap or several openings and gaps. It should also be understood that the openings 646 and gap 648 need not necessarily extend entirely through the keel 640, but may alternatively extend partially therethrough. It should further be understood that the keel 640 need not necessarily define any openings 646 or gaps 648 extending either partially or entirely therethrough. Additionally, although the openings 646 are illustrated as having a circular configuration, it should be understood that other sizes and configurations of openings 646 are also contemplated. As discussed above, the surfaces of the articular component 602 that are in direct contact with vertebral bone may be coated with a bone-growth promoting substance. Specifically, the bearing surface 614 and the surfaces of the keel 640 can be coated with hydroxyapatite to promote bony engagement with the adjacent vertebrae. As also discussed above, the bearing surface 614 and the surfaces of keel 640 can be roughened prior to application of the hydroxyapatite coating.

In one embodiment, the articular component 604 includes a support plate 650 having an articular surface 652 and an opposite bearing surface 654. Support plate 650 may be sized and shaped to substantially correspond to the size and shape of the vertebral endplate of an adjacent vertebra. In one embodiment, the support plate 610 is shaped in a triangular-like configuration to facilitate an oblique insertion approach from either the left or right side of the spine, and as such, includes side portions P4, P5 and P6. The side portions P4, P5 and P6 may take a variety of configurations including curved (illustrated by P5) or straight (illustrated by P4 and P6) configurations. The support plate 650 can include one or more notches 656 or other types of indicia for receiving and engaging with a corresponding portion of a surgical instrument, such as discussed above with reference to articular component 602.

In one embodiment, the articular surface 652 includes a recess 660 having a convex shape, which may be configured as a spherical-shaped socket. However, it should be understood that other configurations of the recess 660 are also contemplated, such as, for example, cylindrical, elliptical or other arcuate configurations or possibly non-arcuate configurations. The remaining portion of the articular surface 652 can be angled or otherwise configured to facilitate the insertion and/or use of the prosthesis.

Although the concave recess 660 is illustrated as having a generally smooth, uninterrupted articular surface, it should be understood that a surface depression or cavity may be defined along a portion of the recess 660 to provide a means for clearing out matter, such as particulate debris, that is disposed between the abutting articular surfaces of components 602, 604. In such case, the convex articular surface of the ball 620 may alternatively define a generally smooth, uninterrupted articular surface. In another embodiment of the invention, each of the convex projection 620 and the concave recess 660 may define a surface depression to facilitate removal of particulate matter disposed between, the abutting articular surfaces.

A flange member or keel 670, configured similar to the keel 640 of articular component 602, extends from the bearing surface 654. In one embodiment, the keel 670 can be centrally located, and is positioned directly or parallel in-line with the keel 640. The keel 640 is straight, but extends along a direction towards the notches 656 and is parallel with one of the side portions P4 of the support plate 650. Such an embodiment accommodates insertion of the prosthetic joint 600 using an oblique approach as opposed to the anterior, lateral, or transforaminal approaches discussed above. In some embodiments, the position of the keel 670 can be offset to help circumvent veins, arteries, bony portions, or other obstacles that may be in place during the insertion of the joint 600.

It should be further understood that other positions, shapes, orientations, and quantities of the keel 670 are also contemplated. It should also be understood that more keels 670 can be used, for similar or additional reasons. Also, the keel 670 may be angled, tapered, or configured in some other shape to facilitate the functional demands of the keel. In still another embodiment, the keel 670 may be configured as a winged keel, including a transverse portion (not shown) extending across the main body portion of keel 670.

In one embodiment, the keel 670 also includes a pair of openings 676 extending therethrough to facilitate bone through-growth to enhance fixation to the adjacent vertebra. Additionally, a gap 678 may also be formed in the keel 670 to further facilitate bone through-growth. The gap 678 also provides a reference point such that an X-ray can be used to evaluate the positioning and alignment of the support plate 604 during insertion of the prosthetic joint 600. It should be understood that any number of openings 676 or gaps 678 may be defined through, keel 670, including a single opening or gap or several openings or gaps. It should also be understood that the openings 676 and gap 678 need not necessarily extend entirely through the keel 670, but may alternatively extend partially therethrough. It should further be understood that the keel 670 need not necessarily define any openings 676 or gaps 678 extending either partially or entirely therethrough. Additionally, although the openings 676 are illustrated as having a circular configuration, it should be understood that other sizes and configurations of openings 676 are also contemplated. As discussed above, the surfaces of the articular component 602 that are in direct contact with vertebral bone are preferably coated with a bone-growth promoting substance. Specifically, the bearing surface 654 and the surfaces of the keel 670 can be coated with hydroxyapatite to promote bony engagement with the adjacent vertebrae. As also discussed above, the bearing surface 654 and the surfaces of keel 670 can be roughened prior to application of the hydroxyapatite coating.

In some embodiments, one or both of the keels 640, 670 may include a sharp forward edge, illustrated by edges 680, 682. By having such an edge, insertion of the keels 640, 670 into the associated vertebral body is facilitated. Also, the edges 680, 682 can be of sufficient sharpness that the vertebral body does not require a slot for receiving the keel 640, 670, discussed in greater detail below.

Figure 43:
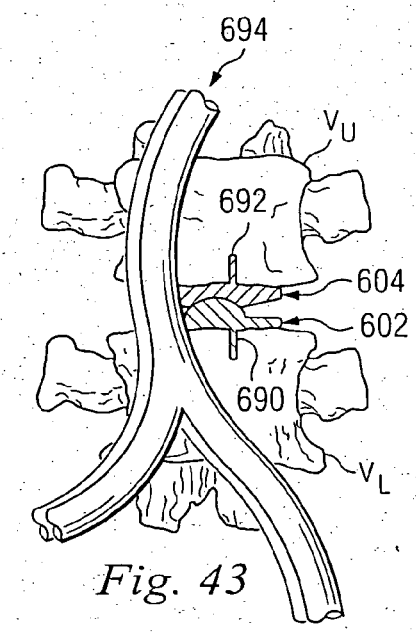
FIG. 43 is a longitudinal, partial sectional view of the prosthetic joint of FIG. 39 disposed between a pair of vertebral endplates.

Referring to FIGS. 42-44a, to accommodate insertion of the prosthetic joint 600 within the intervertebral space, the upper and lower vertebrae $V_U$, $V_L$ can be prepared to accept the prosthetic joint 600 therebetween. Referring specifically to FIG. 43, for the configuration of the prosthetic joint 600 of FIGS. 38-40, multiple slots 690, 692 are formed along the vertebral endplates of the lower vertebrae $V_L$ and the upper vertebrae $V_U$, respectively. The slots 690, 692 can be created by the keels 640, 670 themselves, or can be prepared beforehand by one or more of the methods discussed above. It can be seen from FIGS. 42-44, that if one or more vessels 694 are obstructing a straight anterior approach, the oblique approach will allow for an anterior/lateral insertion. The implant 600 design also ensures a sufficient contact surface for contacting the bony endplates of the vertebrae $V_U$, $V_L$.

Figure 44A:
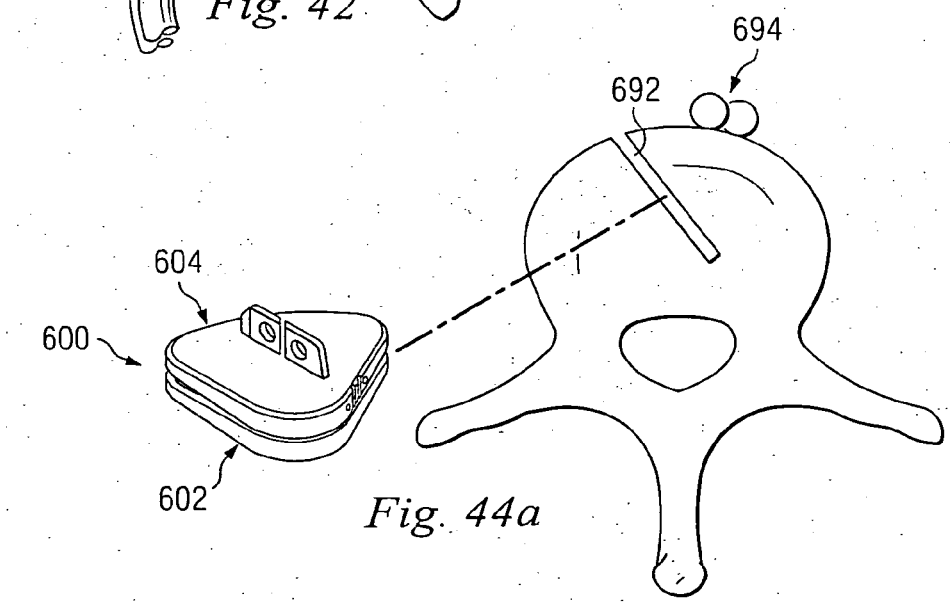
FIG. 44a is a top, schematic view depicting a slot formed in a vertebral endplate for receiving the prosthetic joint of FIG. 39.
Figure 44B:
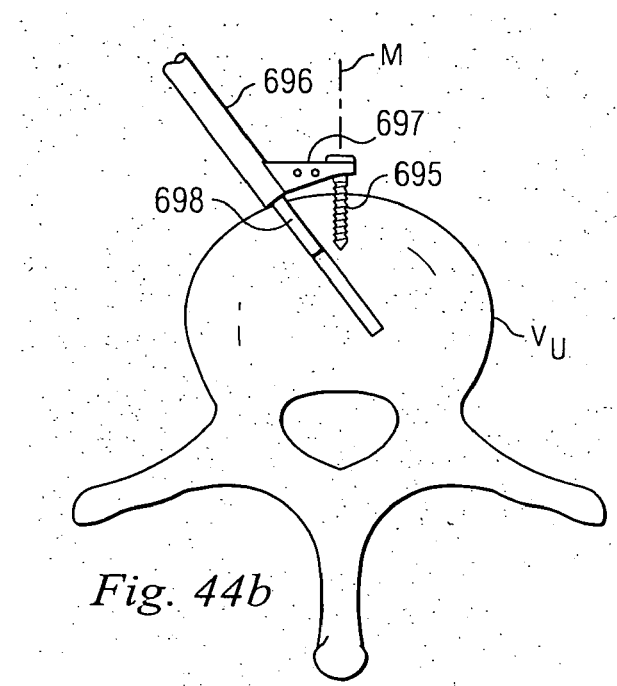
FIG. 44b is a schematic view depicting an alignment process associated with the insertion of the prosthetic joint of FIG. 39.

Referring to FIG. 44b, in one embodiment, the prosthetic joint 600 can be inserted into the intervertebral space via instrumentation such as the guide as disclosed in co-pending application U.S. Ser. No. 10/430,473, which is herein incorporated by reference. In one example of an insertion process for inserting the prosthetic joint 600, the midline M of the vertebrae $V_U$, $V_L$ is located using imaging equipment and a pin 695 is inserted into the upper vertebra $V_U$ along the midline. An oblique guide member 696 is then connected to the pin 695 via a flange 697 and a handle (not shown) associated with the oblique guide member 696 is then adjusted to a proper position. An oblique pin 698 of the oblique guide member 696 is then impacted into the upper vertebra $V_U$ to fix the oblique guide member, thereby indicating the entering reference point and the direction of implant insertion for the prosthetic joint 600. The guide (not shown) can then be used to implant the prosthetic joint 600 into the intervertebral space from an anterior-oblique approach, the details of which are more fully discussed in co-pending application U.S. Ser. No. 10/430,473.

V. Mobile-Bearing Prosthetic Joint

In another embodiment, the above-described prosthetic joints can be modified to provide for translational movement as well as rotational movement. For example, referring to FIGS. 45-47, a mobile-bearing prosthetic joint for anterior insertion is generally referred to by reference numeral 700. It is understood that the mobile-bearing prosthetic joint 700 is described with respect to anterior insertion for the sake of clarity only, and therefore, a variety of insertion directions are contemplated for the mobile-bearing prosthetic joint.

The prosthetic joint 700 extends generally along a longitudinal axis L and includes a first articular component 702 and a second articular component 704. The articular components 702, 704 cooperate to form the prosthetic joint 700 which is sized and configured for disposition within an intervertebral space between a pair of vertebral bodies, such as an intervertebral space S1 between adjacent vertebral bodies $V_S$, $V_I$ (FIG. 48).

The prosthetic joint 700 provides relative pivotal and rotational movement between the adjacent vertebral bodies $V_S$, $V_I$ to maintain or restore motion substantially similar to the normal bio-mechanical motion provided by a natural intervertebral disc but with the added element of translational motion. More specifically, the articular components 702, 704 are permitted to pivot relative to one another about a number of axes, including lateral or side-to-side pivotal movement about a longitudinal axis L and anterior-posterior pivotal movement about a transverse axis T. It should be understood that in one embodiment, the articular components 702, 704 are permitted to pivot relative to one another about any axes that lies in a plane that intersects longitudinal axis L and transverse axis T. Additionally, the articular components 702, 704 are permitted to rotate relative to one another about a rotational axis R. In addition, the articular components 702, 704 are permitted to translate relative to one another as will be further described.

Although the articular components 702, 704 of prosthetic joint 700 may be formed from a wide variety of materials, in one embodiment, the articular components 702, 704 are formed of a cobalt-chrome-molybdenum metallic alloy (ASTM F-799 or F-75). However, in alternative embodiments, the articular components 702, 704 may be formed of other materials such as titanium or stainless steel, a polymeric material such as polyethylene, or any other biocompatible material that would be apparent to one of ordinary skill in the art. The surfaces of the articular components 702, 704 that are positioned in direct contact with vertebral bone may be coated with a bone-growth promoting substance, such as, for example, a hydroxyapatite coating formed of calcium phosphate. Additionally, the surface of the articular components 702, 704 that are positioned in direct contact with vertebral bone may be roughened prior to being coated with the bone-growth promoting substance to further enhance bone on-growth. Such surface roughening may be accomplished by way of, for example, acid etching, knurling, application of a bead coating, or other methods of roughening that would occur to one of ordinary skill in the art.

Articular component 702 includes a support plate 706 having an articular surface 708 and an opposite bearing surface 710. Support plate 706 may be sized and shaped to substantially correspond to the size and shape of the vertebral endplate of an adjacent vertebra. The support plate 706 can include one or more notches 712 or other types of indicia for receiving and engaging with a corresponding portion of a surgical instrument (not shown) to aid in the manipulation and insertion of the articulating joint 700 within an intervertebral space between adjacent vertebrae. The surgical instrument (not shown) is preferably configured to hold the articular components 702, 704 at a predetermined orientation and spatial relationship relative to one another during manipulation and insertion of the articulating joint 700, and to release the articular components 702, 704 once properly positioned between the adjacent vertebrae.

In one embodiment, and referring to FIGS. 49a and 49b, a recess 714 is formed in the articular surface 708. A circumferential edge 716 defining the recess 714 along the articular surface 708 is in a concentric relationship with a recess surface 718, yet has a smaller diameter relative to the recess surface due to a diverging circular side 720 (FIG. 48b) of the recess 714. Although described with reference to having a circular shape, it is understood that the recess 714 may take any number of shapes such as square, triangular, or rectangular shapes.

Referring to FIGS. 50a and 50b, the recess 714 (FIG. 49b) is designed to receive a portion of a modular projection member 722. The projection member 722 includes a flange portion 724, which is shaped to correspond to the shape of the recess 714. As such, the flange portion 724 includes a diverging circumferential side 726, which terminates at a substantially planar engagement surface 728. The engagement surface 728 is adapted to engage the substantially planar recess surface 718 (FIG. 49b). It is understood, however, that although depicted as being substantially planar, the engagement surface 728 and the recess surface 718 may take any number of corresponding shapes. The diameter of the engagement surface 728 is smaller than the diameter of the recess surface 718, thereby allowing translation of the modular projection member 722 relative to the articular component 702.

The remaining portion of the modular projection member 722 is defined by a projection 730 having a convex shape, which may be configured as a spherical-shaped ball (half of which is shown). It should be understood that other configurations of the projection 730 are also contemplated, such as, for example, cylindrical, elliptical or other arcuate configurations or possibly non-arcuate configurations. It should also be understood that the remaining portion of articular surface 708 may take on planar or non-planar configurations, such as, for example, an angular or conical configuration extending about the projection 224.

In one embodiment, the convex articular surface of the projection 730 is interrupted by a surface depression or cavity 732 extending along the projection 730. In one embodiment, the surface depression 732 is configured as a groove. However, it should be understood that other types of surface depressions are also contemplated, including no depression at all. One purpose of the groove 732 is to facilitate the removal of matter disposed between abutting portions of the articular components 702, 704. More specifically, the groove 732 may aid in clearing out matter such as, for example, particulate material, that is disposed between the abutting articular surfaces of components 702, 704.

Figure 45:
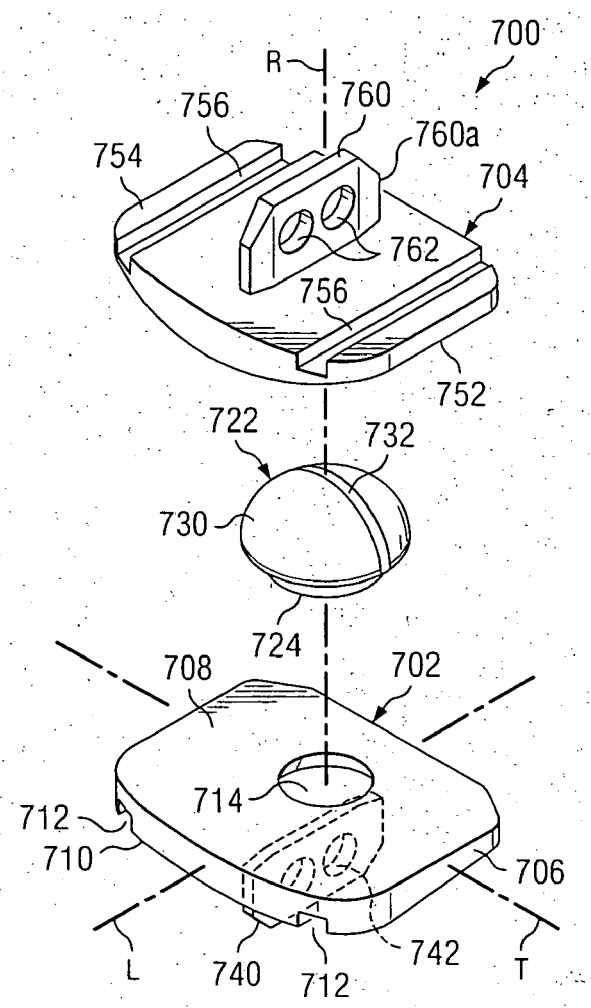
FIG. 45 is an exploded view an alternative prosthetic joint according to yet another embodiment of the present disclosure.
Figure 47:
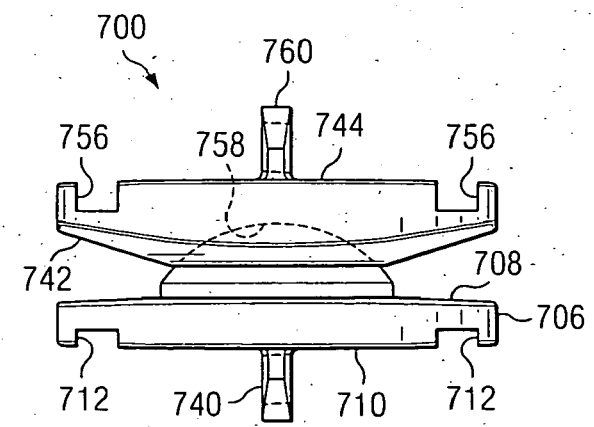
FIG. 47 is a longitudinal view of the prosthetic joint of FIG. 46.

Referring to FIGS. 45 and 49b, a flange member or keel 740 extends from the bearing surface 710 and is configured for disposition within a preformed opening in the adjacent vertebral endplate (such as $V_I$ in FIG. 47). In one embodiment, the keel 740 extends perpendicularly from the bearing surface 710 and is approximately centrally located along the bearing surface 710. However, it should be understood that other positions and orientations of the keel 740 are also contemplated.

In one embodiment, the keel 740 extends along substantially the entire length of the support plate 706. Such an embodiment would accommodate insertion of the articulating joint 700 using an anterior approach. However, as discussed above, other approaches such as lateral, transforaminal, and anterior-oblique approaches are also contemplated for insertion of the prosthetic joint 700. In a further embodiment, the keel 740 may be angled, tapered, or configured in some other shape to facilitate the functional demands of the keel. In still another embodiment, the keel 740 may be configured as a winged keel, including a transverse portion (not shown) extending across the main body portion of keel 740.

The keel 740 also includes a pair of openings 742 extending therethrough to facilitate bone through-growth to enhance fixation to the adjacent vertebra. However, it should be understood that any number of openings 742 may be defined through keel 740, including a single opening or three or more openings. It should also be understood that the openings 742 need not necessarily extend entirely through the keel 740, but may alternatively extend partially therethrough. It should further be understood that the keel 740 need not necessarily define any openings 742 extending either partially or entirely therethrough. Additionally, although the openings 742 are illustrated as having a circular configuration, it should be understood that other sizes and configurations of the openings 742 are also contemplated. As discussed above, the surfaces of the articular component 702 that are in direct contact with vertebral bone are preferably coated with a bone-growth promoting substance. Specifically, the bearing surface 710 and the surfaces of the keel 740 can be coated with hydroxyapatite to promote bony engagement with the adjacent vertebrae. As also discussed above, the bearing surface 710 and the surfaces of keel 740 can be roughened prior to application of the hydroxyapatite coating.

Figure 46:
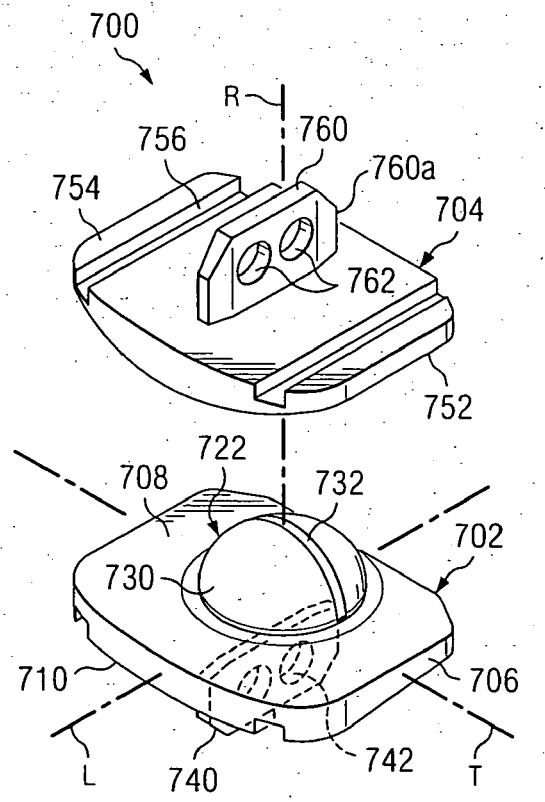
FIG. 46 is an isometric view of the prosthetic joint of FIG. 45.

Referring to FIGS. 45-47, in one embodiment, the articular component 704 includes a support plate 750 having an articular surface 752 and an opposite bearing surface 754. Support plate 750 may be sized and shaped to substantially correspond to the size and shape of the vertebral endplate of an adjacent vertebra. The support plate 750 can include one or more notches 756 or other types of indicia for receiving and engaging with a corresponding portion of a surgical instrument, such as discussed above with reference to articular component 702.

In one embodiment, the articular surface 752 includes a recess 758 (FIG. 47), which has a convex shape, such as that of a spherical-shaped socket. However, it should be understood that other configurations of the recess 758 are also contemplated, such as, for example, cylindrical, elliptical or other arcuate configurations or possibly non-arcuate configurations. The remaining portion of the articular surface 752 can be angled or otherwise configured to facilitate the insertion and/or use of the articulating joint 700.

Although the concave recess 758 is illustrated as having a generally smooth, uninterrupted articular surface, it should be understood that a surface depression or cavity may be defined along a portion of the recess 758 to aid in clearing out matter, such as particulate debris, that is disposed between the abutting articular surfaces of articular components 702, 704. In such case, the convex articular surface of the projection 730 may alternatively define a generally smooth, uninterrupted articular surface. In another embodiment, each of the convex projection 730 and the concave recess 758 may define a surface depression to facilitate removal of particulate matter disposed between the abutting articular surfaces.

A flange member or keel 760, configured similar to the keel 740 of articular component 702, extends from the bearing surface 754. In one embodiment, the keel 760 extends perpendicularly from the bearing surface 754 and is approximately centrally located along bearing surface 754. However, it should be understood that other positions and orientations of the keel 760 are also contemplated; It should also be understood that the articular component 704 may include two or more keels 760 extending from the bearing surface 754.

In one embodiment, the keel 760 extends along substantially the entire length of the support plate 750. Such an embodiment would accommodate insertion of the prosthetic joint 700 using an anterior approach. However, as discussed above, other approaches such as lateral, transforaminal, and anterior-oblique approaches are also contemplated for insertion of the prosthetic joint 700. In a further embodiment, the keel 760 may be angled, tapered, or configured in some other shape to facilitate the functional demands of the keel. In still another embodiment, the keel 760 may be configured as a winged keel, including a transverse portion (not shown) extending across the main body portion of keel 760.

The keel 760 also includes a pair of openings 762 extending therethrough to facilitate bone through-growth to enhance fixation to the adjacent vertebra. However, it should be understood that any number of openings 762 may be defined through keel 760, including a single opening or three or more openings. It should also be understood that the openings 762 need not necessarily extend entirely through the keel 760, but may alternatively extend partially therethrough. It should further be understood that the keel 760 need not necessarily define any openings 762 extending either partially or entirely therethrough. Additionally, although the openings 762 are illustrated as having a circular configuration, it should be understood that other sizes and configurations of openings 762 are also contemplated. As discussed above, the surfaces of the articular component 704 that are in direct contact with vertebral bone are preferably coated with a bone-growth promoting substance. Specifically, the bearing surface 754 and the surfaces of the keel 760 can be coated with hydroxyapatite to promote bony engagement with the adjacent vertebrae. As also discussed above, the bearing surface 754 and the surfaces of keel 760 can be roughened prior to application of the hydroxyapatite coating.

In some embodiments, one or both of the keels 740, 760 may include a sharp forward edge, illustrated by edge 760a of FIGS. 45 and 46. By having such an edge, insertion of the keel 740, 760 into the associated vertebral body is facilitated. Also, the edge 760a can be of sufficient sharpness that the vertebral body does not require a slot for receiving the keel 760, discussed in greater detail below.

Referring to FIG. 45, the mobile-bearing prosthetic joint 700 is assembled by inserting the modular projection 722 member into the recess 714 formed in the articular surface 708 of articular component 702. Upon assemblage, the prosthetic joint 700 is ready to be inserted into the disc space S1 between adjacent vertebral bodies $V_S$, $V_I$ (FIG. 48).

Referring to FIG. 48, to accommodate insertion of the prosthetic joint 700 within the intervertebral space S1, the adjacent vertebral bodies $V_S$, $V_I$ can be prepared to accept the prosthetic joint 700 therebetween. For the configuration of the prosthetic joint 700 of FIGS. 45-47, slots 770, 772 are formed along the vertebral endplates of the vertebrae $V_S$ and the vertebrae $V_I$, respectively. The slots 770, 772 can be created by the keels 740, 760 themselves, or can be prepared beforehand by one or more of the methods discussed above.

Upon insertion into the disc space S1, the prosthetic joint 700 allows translational movement of the articular component 704 relative to the articular component 702 due to the engagement of the modular projection 722 with the concave recess 758 of articular component 704. For example, in FIG. 51, the modular projection member 722 is shown in a posterior position (which would result in movement of the articular component 704 in the posterior direction P), while in FIG. 52, the modular projection member 722 is shown in an anterior position (which would result in movement of the articular component 704 in the anterior direction A). FIGS. 51 and 52 are of course only exemplary of the translational movement allowed by the implementation of modular projection member 722 and the corresponding recess 714, and thus, the amount of translational movement of the modular projection member 722, and therefore the articular component 704, relative to the articular component 702 can vary, including in directions other than P and A.

Furthermore, the positioning of the modular projection member 722 within the recess 714 of the articular component 702 allows the modular projection to spin relative to the articular component 702. Thus, in such an embodiment, the modular projection member 722 adds the benefit of being able to impart rotation to the articular component 704 (via the engagement with the recess 758) independent of translational movement imparted to the articular component 704. Such independent relationship between translational and rotational movement adds to the amount of mobility experienced at the prosthetic joint 700 relative to prosthetic joints for which translational movement is dependent upon rotational movement and vice versa.

The present disclosure has been described relative to several preferred embodiments. Improvements or modifications that become apparent to persons of ordinary skill in the art after reading this disclosure are deemed within the spirit and scope of the application. For example, the articulating components of the above-described articulating joints may be reversed without departing from certain aspects of the disclosure. Accordingly, it is understood that several modifications, changes and substitutions are intended in the foregoing disclosure and, in some instances, some features of the disclosure will be employed without a corresponding use of other features. It is also understood that all spatial references, such as "longitudinal" and "transverse," are for illustrative purposes only and can be varied within the scope of the disclosure. Accordingly, it is appropriate that the appended claims be construed broadly and in a manner consistent with the scope of the disclosure.

What is claimed is:

1. A method for treating spondylolisthesis from an anterior approach, comprising
    providing a prosthetic device having a first articular component with an offset projection, and a second articular component with an offset recess adapted to engage with the offset projection such that the first articular component is offset relative to the second articular component to accommodate a spondylosed relationship,
    longitudinally inserting the first articular component into a disc space such that a portion of the first articular component engages a first vertebra, and
    longitudinally inserting the second articular component into the disc space such that the offset projection and offset recess are engaged with one another and such that a portion of the second articular component engages a second vertebra, the second vertebra being adjacent to and in a spondylosed relationship with the first vertebra.

2. The method of claim 1 wherein the projection extends from a first surface of the first articular component, the projection being offset in a first direction relative to the first surface of the first articular component.

3. The method of claim 2 wherein the recess is formed in a second surface of the second articular component, the recess being offset in a second direction relative to the second surface of the second articular component, the second direction being substantially opposite the first direction.

4. The method of claim 1, wherein longitudinally inserting the first articular component and longitudinally inserting the second articular component occurs simultaneously.

* * * * *

UNITED STATES PATENT AND TRADEMARK OFFICE
CERTIFICATE OF CORRECTION

PATENT NO. : 7,850,735 B2
APPLICATION NO. : 10/774135
DATED : December 14, 2010
INVENTOR(S) : Eisermann et al.

It is certified that error appears in the above-identified patent and that said Letters Patent is hereby corrected as shown below:

On the Title Page, in Item (75), under "Inventors", in Column 1, Line 3, delete "Mathews" and insert -- Matthews --, therefor.

On Title Page 2, in Item (56), under "OTHER PUBLICATIONS", in Column 2, Line 30, delete "Cambell's" and insert -- Campbell's --, therefor.

In Column 4, Line 29, delete "verterbral" and insert -- vertebral --, therefor.

In Column 4, Line 32, delete "verterbral" and insert -- vertebral --, therefor.

In Column 4, Line 35, delete "verterbral" and insert -- vertebral --, therefor.

In Column 17, Line 52, delete "to," and insert -- to --, therefor.

In Column 25, Line 64, delete "160" and insert -- 610 --, therefor.

In Column 27, Line 52, delete "between," and insert -- between --, therefor.

In Column 28, Line 19, delete "through," and insert -- through --, therefor.

In Column 32, Line 14, delete "contemplated;" and insert -- contemplated. --, therefor.

Signed and Sealed this
Twenty-sixth Day of April, 2011

David J. Kappos
*Director of the United States Patent and Trademark Office*